US00RE48163E

(19) United States
(12) Reissued Patent
Primiano et al.

(10) Patent Number: US RE48,163 E
(45) Date of Reissued Patent: Aug. 18, 2020

(54) SURGICAL REAMING INSTRUMENT FOR SHAPING A BONE CAVITY

(71) Applicant: Howmedica Osteonics Corp., Mahwah, NJ (US)

(72) Inventors: Steven Primiano, Holmdel, NJ (US); Damon J. Servidio, Towaco, NJ (US); Mark Mooradian, San Diego, CA (US); Jeffery Arnett, Gilbert, AZ (US)

(73) Assignee: Howmedica Osteonics Corp., Mahwah, NJ (US)

(21) Appl. No.: 15/972,333

(22) Filed: May 7, 2018

Related U.S. Patent Documents

Reissue of:
(64) Patent No.: 9,011,444
Issued: Apr. 21, 2015
Appl. No.: 13/708,491
Filed: Dec. 7, 2012

U.S. Applications:
(62) Division of application No. 15/493,542, filed on Apr. 21, 2017, now Pat. No. Re. 47,149, which is an application for the reissue of Pat. No. 9,011,444.
(Continued)

(51) Int. Cl.
*A61B 17/16* (2006.01)
*A61F 2/38* (2006.01)
(Continued)

(52) U.S. Cl.
CPC ..... *A61B 17/16* (2013.01); *A61B 17/1675* (2013.01); *A61B 17/17* (2013.01); *A61B 17/1764* (2013.01); *A61F 2/389* (2013.01); *A61F 2/4684* (2013.01)

(58) Field of Classification Search
CPC ..... A61B 17/16; A61B 17/17; A61B 17/1675; A61B 17/1764; A61F 2/3859; A61F 2/389; A61F 2/30734; A61F 2/4684
(Continued)

(56) References Cited

U.S. PATENT DOCUMENTS 3,859,669 A 1/1975 Shersher et al.
3,924,274 A 12/1975 Heimke et al.
(Continued)

FOREIGN PATENT DOCUMENTS

DE 2842847 A1 1/1980
DE 2842847 A1 4/1980
(Continued)

OTHER PUBLICATIONS

Schreurs, et al., Femoral Component Revision with Use of Impaction Bone-Grafting and a Cemented Polished Stem. Surgical Technique, The Journal of Bone & Joint Surgery, Sep. 2006, pp. 259-274.
(Continued)

*Primary Examiner* — Beverly M Flanagan
(74) *Attorney, Agent, or Firm* — Lerner, David, Littenberg, Krumholz & Mentlik, LLP

(57) ABSTRACT

Disclosed herein are systems and methods for shaping bone voids during revision procedures of total knee replacements. The systems disclosed herein generally include a cannulated reamer assembly, a reaming guide assembly, a guide tube assembly, a trial stem assembly, and an optional insertion/removal tool. Metaphyseal reconstruction devices can be used to fill the bone voids in conjunction with the systems and methods disclosed herein.

12 Claims, 25 Drawing Sheets

(Amended)

Related U.S. Application Data

(60) Provisional application No. 61/568,808, filed on Dec. 9, 2011.

(51) Int. Cl.
*A61B 17/17* (2006.01)
*A61F 2/46* (2006.01)
*A61F 2/30* (2006.01)

(58) Field of Classification Search
USPC ..... 623/18.11, 20.14, 20.16, 20.32, 23.48
See application file for complete search history.

(56) References Cited

U.S. PATENT DOCUMENTS 3,979,778 A 9/1976 Stroot
3,986,212 A 10/1976 Sauer
4,045,825 A 9/1977 Stroot
4,045,826 A 9/1977 Stroot
4,065,817 A 1/1978 Branemark et al.
4,306,550 A 12/1981 Forte
4,341,206 A 7/1982 Perrett et al.
4,355,427 A 10/1982 Schneider
4,463,444 A 7/1984 Daniels et al.
4,549,319 A 10/1985 Meyer
4,681,589 A 7/1987 Tronzo
4,693,721 A 9/1987 Ducheyne
4,714,475 A 12/1987 Grundei et al.
4,728,335 A 3/1988 Jurgutis
4,735,625 A 4/1988 Davidson
4,738,256 A 4/1988 Freeman et al.
4,751,922 A 6/1988 DiPietropolo
4,777,942 A 10/1988 Frey et al.
4,790,852 A 12/1988 Noiles
4,822,366 A 4/1989 Bolesky
4,846,839 A 7/1989 Noiles
5,011,496 A 4/1991 Forte et al.
5,035,717 A 7/1991 Brooks
5,047,033 A 9/1991 Fallin
5,049,157 A 9/1991 Mittelmeier et al.
5,061,287 A 10/1991 Feiler
5,122,134 A 6/1992 Borzone et al.
5,152,797 A 10/1992 Luckman et al.
5,190,548 A 3/1993 Davis
5,192,283 A 3/1993 Ling et al.
5,342,363 A 8/1994 Richelsoph
5,342,366 A 8/1994 Whiteside et al.
5,358,526 A 10/1994 Tornier
5,387,218 A 2/1995 Meswania
5,403,320 A 4/1995 Luman et al.
5,411,505 A 5/1995 Mumme
5,445,642 A 8/1995 McNulty et al.
5,480,453 A 1/1996 Burke
5,489,311 A 2/1996 Cipolletti
5,496,324 A 3/1996 Barnes
5,527,316 A 6/1996 Stone et al.
5,534,005 A 7/1996 Tokish, Jr. et al.
5,540,694 A 7/1996 DeCarlo, Jr. et al.
5,591,233 A 1/1997 Kelman et al.
5,634,927 A 6/1997 Houston et al.
5,649,299 A 7/1997 Battin et al.
5,702,486 A 12/1997 Craig et al.
5,741,335 A 4/1998 Gerber et al.
5,755,720 A 5/1998 Mikhail
5,755,793 A 5/1998 Smith et al.
5,782,921 A 7/1998 Colleran et al.
5,824,097 A 10/1998 Gabriel et al.
5,931,841 A 8/1999 Ralph
5,944,758 A 8/1999 Mansat et al.
5,951,603 A 9/1999 O'Neil et al.
5,957,925 A 9/1999 Cook et al.
5,976,145 A 11/1999 Kennefick, III
5,976,147 A 11/1999 LaSalle et al.
5,984,968 A 11/1999 Park
5,989,257 A * 11/1999 Tidwell et al. ..... 606/79
5,993,455 A 11/1999 Noble
6,010,534 A 1/2000 O'Neil et al.
6,053,945 A 4/2000 O'Neil et al.
6,071,311 A 6/2000 O'Neil et al.
6,127,596 A 10/2000 Brown et al.
6,139,584 A 10/2000 Ochoa et al.
6,152,963 A 11/2000 Noiles et al.
6,171,342 B1 1/2001 O'Neil et al.
6,214,052 B1 4/2001 Burkinshaw
6,214,053 B1 4/2001 Ling et al.
6,228,120 B1 5/2001 Leonard et al.
6,241,722 B1 6/2001 Dobak et al.
6,245,113 B1 6/2001 Revie et al.
6,264,699 B1 7/2001 Noiles et al.
6,283,999 B1 9/2001 Rockwood, Jr.
6,398,812 B1 6/2002 Masini
6,406,496 B1 6/2002 Ruter
6,440,171 B1 8/2002 Doubler et al.
6,494,913 B1 12/2002 Huebner
6,520,994 B2 2/2003 Nogarin
6,558,425 B2 5/2003 Rockwood, Jr.
6,592,622 B1 7/2003 Ferguson
6,702,822 B1 3/2004 Noiles et al.
6,887,276 B2 5/2005 Gerbec et al.
6,905,513 B1 6/2005 Metzger
6,945,556 B2 9/2005 Maertens
7,001,429 B2 2/2006 Ferguson
7,070,622 B1 7/2006 Brown et al.
7,074,224 B2 7/2006 Daniels et al.
7,090,677 B2 8/2006 Fallin et al.
7,108,719 B2 9/2006 Horber
7,175,664 B1 2/2007 Lakin
7,255,702 B2 8/2007 Serra et al.
7,291,174 B2 11/2007 German et al.
7,297,163 B2 11/2007 Huebner
7,338,528 B2 3/2008 Stone et al.
7,393,355 B2 7/2008 Tulkis et al.
7,462,197 B2 12/2008 Tornier et al.
7,481,814 B1 1/2009 Metzger
7,507,256 B2 3/2009 Heck et al.
7,537,664 B2 5/2009 O'Neill et al.
7,556,652 B2 7/2009 Angibaud et al.
7,615,080 B2 11/2009 Ondrla
7,785,328 B2 8/2010 Christie et al.
7,799,085 B2 9/2010 Goodfried et al.
7,892,288 B2 2/2011 Blaylock et al.
7,892,290 B2 2/2011 Bergin et al.
7,918,892 B2 4/2011 Huebner
7,942,879 B2 5/2011 Christie et al.
8,029,573 B2 10/2011 Podolsky
8,105,385 B2 1/2012 Maroney et al.
8,118,868 B2 2/2012 May et al.
8,147,861 B2 4/2012 Jones et al.
8,167,882 B2 5/2012 Sackett et al.
8,177,788 B2 5/2012 McLean et al.
8,177,849 B2 5/2012 Meyers et al.
8,182,542 B2 5/2012 Ferko
8,187,336 B2 5/2012 Jamali
8,192,497 B2 6/2012 Ondrla
8,226,725 B2 7/2012 Ferko
8,350,186 B2 1/2013 Jones et al.
8,372,157 B2 2/2013 Petersen et al.
8,382,849 B2 2/2013 Thomas
8,424,183 B2 4/2013 Thomas
8,444,699 B2 5/2013 Metzger et al.
8,460,393 B2 6/2013 Smith et al.
8,506,645 B2 8/2013 Blaylock et al.
8,585,770 B2 11/2013 Meridew et al.
8,636,800 B2 1/2014 Ferko et al.
8,715,356 B2 5/2014 Porter et al.
8,790,402 B2 * 7/2014 Monaghan ..... A61L 27/04 623/16.11
8,900,317 B2 12/2014 Zubok et al.
9,011,444 B2 4/2015 Primiano et al.
2003/0171756 A1 9/2003 Fallin et al.
2003/0171815 A1 9/2003 Kana et al.
2003/0187449 A1 10/2003 McCleary et al.
2004/0049285 A1 3/2004 Haas

(56) References Cited

U.S. PATENT DOCUMENTS

| | | | | |
|---|---|---|---|---|
| 2004/0162619 | A1 | 8/2004 | Blaylock et al. | A61B 17/1764 623/20.16 |
| 2004/0267267 | A1 | 12/2004 | Daniels et al. | |
| 2005/0090902 | A1 | 4/2005 | Masini | |
| 2005/0177241 | A1 | 8/2005 | Angibaud et al. | |
| 2005/0288676 | A1 | 12/2005 | Schnieders et al. | |
| 2006/0041317 | A1 | 2/2006 | Hazebrouck et al. | |
| 2006/0147332 | A1 | 7/2006 | Jones et al. | |
| 2007/0088443 | A1 | 4/2007 | Hanssen et al. | |
| 2007/0118229 | A1 | 5/2007 | Bergin et al. | |
| 2007/0142914 | A1 | 6/2007 | Jones et al. | |
| 2007/0162033 | A1 | 7/2007 | Daniels et al. | |
| 2008/0051908 | A1* | 2/2008 | Angibaud | A61F 2/389 623/20.32 |
| 2008/0281428 | A1 | 11/2008 | Meyers et al. | |
| 2009/0157190 | A1 | 6/2009 | Collazo et al. | |
| 2010/0057212 | A1* | 3/2010 | Thomas | A61F 2/30734 623/20.32 |
| 2010/0076565 | A1 | 3/2010 | Thomas | |
| 2010/0082031 | A1* | 4/2010 | Sackett et al. | 606/79 |
| 2010/0114323 | A1* | 5/2010 | Deruntz et al. | 623/20.21 |
| 2010/0222891 | A1 | 9/2010 | Goodfried et al. | |
| 2011/0009973 | A1 | 1/2011 | Meyers et al. | |
| 2011/0009974 | A1 | 1/2011 | Blaylock et al. | |
| 2011/0015634 | A1 | 1/2011 | Smith et al. | |
| 2011/0130840 | A1 | 6/2011 | Oskouei | |
| 2011/0190899 | A1 | 8/2011 | Pierce et al. | |
| 2011/0213467 | A1 | 9/2011 | Lozier et al. | |
| 2012/0016482 | A1 | 1/2012 | Mooradian et al. | |
| 2012/0089146 | A1 | 4/2012 | Ferko et al. | |
| 2012/0226281 | A1 | 9/2012 | Sackett et al. | |
| 2012/0310361 | A1* | 12/2012 | Zubok | A61F 2/30734 623/20.32 |
| 2013/0053976 | A1 | 2/2013 | Gugler et al. | |
| 2013/0172892 | A1 | 7/2013 | Servidio et al. | |
| 2013/0211536 | A1 | 8/2013 | Metzger et al. | |
| 2013/0264749 | A1 | 10/2013 | Jones et al. | |

FOREIGN PATENT DOCUMENTS

| | | | |
|---|---|---|---|
| EP | 0016480 | A1 | 10/1980 |
| EP | 2168586 | A1 | 3/2010 |
| EP | 2181071 | A1 | 5/2010 |
| EP | 2181672 | A1 | 5/2010 |
| GB | 2159416 | A | 12/1985 |
| WO | 03094698 | A2 | 11/2003 |
| WO | 2006127486 | A2 | 11/2006 |
| WO | 2008069800 | A1 | 6/2008 |

OTHER PUBLICATIONS

Lonner, et al., Impaction Grafting and Wire Mesh for Uncontained Defects in Revision Knee Arthroplasty, Clinical Orthopaedics and Related Research, No. 404, pp. 145-151, Copyright Nov. 2002, Lippincott Williams & Wilkins, Inc.

Stryker Howmedica Osteonics, X-change Revision Instruments System, Copyright Howmedica Osteonics, Sep. 2001.

U.S. Appl. No. 13/441,154, filed Apr. 6, 2012.

International Search Report and Written Opinion for Application No. PCT/US2012/072087 dated May 2, 2013.

Extended European Search Report for Application No. EP14159399 dated Jun. 6, 2014.

Partial International Search Report dated Mar. 15, 2013 for Application No. PCT/US2012/072087.

International Search Report and Written Opinion for Application No. PCT/US2012/068473 dated Mar. 8, 2013.

Schreurs, et al., Femoral Component Revision with Use of Impaction Bone-Grafting and a Cemented Polished Stem. Surgical Technique, The Journal of Bone & Joint Surgery, 2006, pp. 259-274.

Knee Revision Product Portfolio, DePuy International Ltd., a Johnson & Johnson Company, Cat. No. 9075-40-000 version 1, Copyright 2009.

Zimmer, Trabecular Metal, Tibial and Femoral Cones Surgical Techniques, Copyright 2011.

* cited by examiner

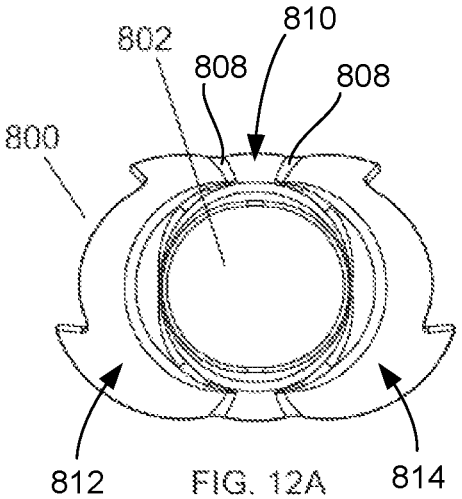
FIG. 12A
(Amended)
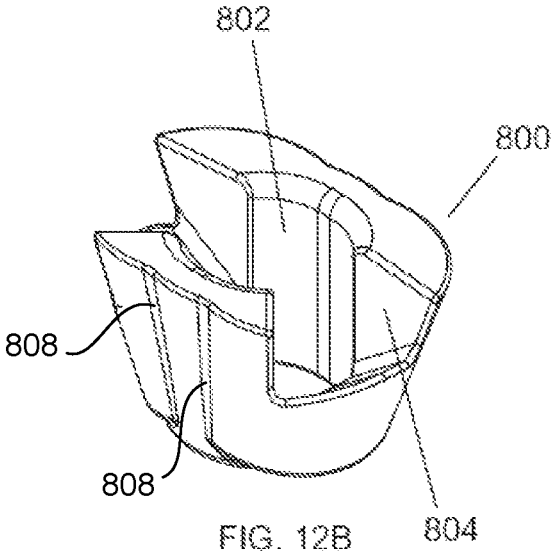
FIG. 12B
(Amended)
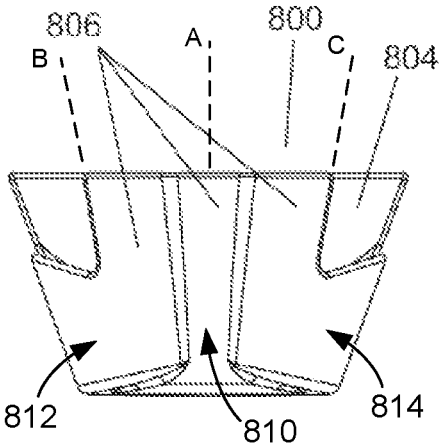
FIG. 12C
(Amended)

SURGICAL REAMING INSTRUMENT FOR SHAPING A BONE CAVITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED [APPLICATION] *APPLICATIONS*

This application *is a reissue divisional of U.S. application Ser. No. 15/493,542, filed on Apr. 21, 2017, which is an application for reissue of U.S. Pat. No. 9,011,444. U.S. Pat. No. 9,011,444* claims the benefit of the filing date of U.S. Provisional Patent Application No. 61/568,808, filed Dec. 9, 2011, the disclosure of which is hereby incorporated [herein] by reference.

FIELD OF THE INVENTION

The present invention relates to surgical instruments for preparing a bone to receive a joint prosthesis system, and in particular relates to fully guided surgical reaming instruments for use in total knee replacement revision procedures.

BACKGROUND OF THE INVENTION

Joint replacement surgery is a common orthopedic procedure for joint such as the shoulder, hip, knee, ankle and wrist. Prior to implanting prosthetic components in a joint of a patient, a surgeon generally has to resect at least a portion of the patient's native bone in order to create a recess or cavity for receiving at least a portion of the prosthetic components being implanted. During the process of resecting bone, a surgeon generally only resects the amount of bone that is needed in order to implant the prosthetic components in the joint replacement surgery properly. Once native bone is resected from a joint, it generally can no longer be used in the joint. Thus, the surgeon attempts to maintain as much native structural integrity of the joint as he or she can during the resection process.

When prosthetic components fail for any one of a variety of reasons, a revision procedure is often necessary. An issue generally encountered by surgeons replacing joints during a revision procedure is the loss of native bone near the joint being replaced. Defects in a bone adjacent a joint, such as the hip or knee, may occur due to wear and arthritis of the joint, congenital deformity, and following the removal of a failed prosthetic component. When the failed prosthetic component or components are removed from the joint during a revision procedure, it is common for there to have been further native bone loss in the area adjacent the original implant position of the prosthetic component or components. This bone loss is typically due to movement of the component or components after implantation or even degeneration or further degeneration of the bone, which can form bone voids that have unpredictable and non-uniform shapes.

When bone voids are observed in either the proximal tibia or distal femur, or both, it is standard surgical practice to fill those voids as part of the surgical procedure. The preferred practice is to fill those voids with weight bearing void fillers, typically made of an implant-grade metal such as titanium. These void fillers may be referred to as metaphyseal reconstruction devices (MRD). The name MRD more accurately reflects functions such as weight bearing that these devices provide.

Because the bone voids are typically irregular in shape, preparation of the bone void area is typically required prior to implantation of the MRD. This preparation (typically by reaming, broaching or milling) ensures there is sufficient room in the bone cavity for the MRD. An accurate fit between the shaped bone cavity and the MRD is important for establishing joint line, and allowing for weight bearing and bone remodeling during the recovery process.

Different methods are commonly used to attempt to prepare the bone void area to create an accurate fit between the shaped bone cavity and the MRD. One method is to ream along the intramedullary (IM) axis, followed by broaching. Another method is to ream on the IM axis, followed by freehand burr or rongeur bone removal, which may also be followed by broaching. Problems with these methods include that reaming is performed on the IM axis only, so that void areas at a distance from the IM axis, which commonly occur, can only be resected using manual methods. Moreover, broaching generally has at least two problems. First, a manual operation can be time consuming, particularly in cases of sclerotic bone, which exposes the patient to an increased risk of infection and a longer recovery. Second, in the case of large bone voids, broaching generally needs to be performed in a multi-step process because attempting to remove high volumes of bone in a single broaching step generally requires high impact forces to the bone. Also, freehand bone removal, either powered or unpowered, such as by burr or rongeur, often does not produce accurate cavity shapes to receive predefined prosthetic components. A typical result is that areas remain where the outer walls of the MRD do not contact the cavity, which may lead to undesirable stress distribution and possible loss of bone regrowth. Also typical is the time consuming requirement of iterative bone removal, with multiple checks against the MRD, to obtain a correct fit.

Thus, there is a need for a surgical reaming instrument that creates accurate bone cavity geometries in minimal time and that minimizes the necessity for freehand bone removal. There is also a need for enabling surgeons to create bone cavities with a fully guided system.

BRIEF SUMMARY OF THE INVENTION

According to one aspect of the present invention, a surgical system for preparing a bone. The surgical system comprises a reaming guide assembly, which includes a trial stem having a proximal end and a longitudinal axis. The trial stem is configured to fit into an intramedullary canal in the bone. The reaming guide assembly also comprises a guide tube assembly, which has a distal end portion and a guide tube that is angled with respect to the distal end portion, wherein the distal end portion of the guide tube is coupled to the proximal end of the trial stem such that a longitudinal axis of the guide tube is angled with respect to the longitudinal axis of the trial stem. The surgical system further comprises a cannulated reamer assembly for shaping a bone cavity. The cannulated reamer assembly has a proximal end, a reaming head coupled at a distal end and a cannulation extending through the reaming head and distal end thereof, wherein a longitudinal axis of the cannulated reamer assembly is angled with respect to the longitudinal axis of the trial stem when at least a portion of the guide tube is housed within the cannulation of the cannulated reamer assembly.

In one embodiment, the proximal end of the cannulated reamer assembly is configured to engage a torque applying device, for example a drill or manual device.

According to another embodiment, the cannulated reamer assembly further comprises a quick connect mechanism, which has a ball detent engaged to a distal end of a reamer shaft. The ball detent selectively engages a notch in a proximally protruding extension of the reaming head in order to couple the reamer shaft to the reamer head.

According to another aspect of the present invention, the reaming guide assembly further comprises a handle assembly for manipulating the reaming guide assembly. The handle assembly is coupled to the proximal end of the trial stem such that a surgeon can manipulate the reaming guide assembly while the trial stem is located in the intramedullary canal.

Yet another aspect of the current invention the surgical system further comprises an insertion/removal tool for efficient removal of the reaming guide assembly from the bone canal. The insertion/removal tool has a distal end configured for selective engagement to the proximal end of the trial stem.

In one embodiment, the guide tube assembly and the handle assembly are fixed with respect to each other and are rotatably mounted to the proximal end of the trial stem such that a surgeon may rotate the guide tube assembly and the handle assembly about the longitudinal axis of the trial stem while the guide tube assembly and the handle assembly partially reside within a central pocket in the bone.

According to another aspect of the current invention, the surgical system further comprises a tibial implant for implantation into the reamed bone void created by the reaming guide and cannulated reamer assemblies. The tibial implant is shaped to match contours of the bone cavity and has a central opening defined therethrough, wherein the central opening is configured to permit the passage of the trial stem or a stem boss of a tibial baseplate into the intramedullary canal.

The shape of the tibial implant may be realized in the form of at least two outer surfaces being blended tapered conical surfaces that substantially match the contours of the bone cavity.

In one embodiment, the tibial implant further comprises a proximal surface, a lateral wall, a medial wall and a fin clearance for positional adjustment of the tibial baseplate. The fin clearance defines a groove that extends from the lateral wall through the medial wall and extends through the proximal surface.

According to another embodiment of the present invention, the surgical system further comprises a femoral implant for implantation into the bone cavity. The femoral implant is shaped to match contours of the bone cavity and having a central opening defined therethrough, wherein the central opening is configured to permit the passage of a femoral stem into the intramedullry canal.

The shape of the femoral implant may be realized in the form of at least two outer surfaces being tapered conical surfaces that substantially match the contours of the bone cavity.

In one embodiment, the femoral implant further comprises a posterior wall, an anterior wall and a first and second clearance space, wherein the first clearance space defines a recess in the posterior wall shaped to accommodate a femoral cam box, and the second clearance space defines a cut in anterior wall shaped to accommodate an anterior chamfer of a femoral implant.

Another aspect of the present invention is a surgical method for preparing bone. The method comprises placing a reaming guide assembly at least partially into an already formed intramedullary canal and an already formed central pocket. The central pocket is in fluid communication with the intramedullary canal. The reaming guide assembly comprises a trial stem and guide tube assembly. The trial stem has a proximal end configured to be received in the intramedullary canal, and the guide tube assembly has a distal end portion coupled to the proximal end of the trial stem and a guide tube angled with respect to the distal end portion. The guide tube assembly at least partially resides in the central pocket when the trial stem is fully seated in the intraumeddulary canal. The method further comprises coupling a cannulated reamer assembly to the guide tube assembly such that the proximal end of the guide tube assembly is housed within a cannulation of the cannulated reamer assembly, and the reaming head contacts bone at a first position. Further, there is a step of driving the cannulated reamer to a predetermined depth into the bone, thereby forming a first bone cavity adjacent to the central pocket.

In one embodiment, the reaming guide assembly further comprises a handle assembly. The handle assembly being fixed at the proximal end of the trial stem such that the handle assembly at least partially resides in the central pocket when the trial stem is fully seated in the intramedullary canal.

A further aspect of the method comprises the step of manipulating the handle assembly, thereby placing the reaming guide assembly in an optimum angular position.

In yet another embodiment, the guide tube assembly and the handle assembly are fixed with respect to each other and are rotatably mounted to the proximal end of the trial stem.

According to an additional aspect of the method, the method further comprises the step of rotating the handle assembly and guide tube assembly to a second position while partially residing within the central pocket.

In one embodiment, the method includes a step of reaming bone at the second position with the cannulated reamer assembly placed over the guide tube assembly, thereby forming a second bone cavity adjacent to the central pocket.

According to another embodiment, is a method for preparing bone to receive a revision prosthesis, which comprises the step of reaming bone generally along an intramedullary canal with an intramedullary reamer having a proximal end. Another step of the method is placing a cannulated reamer assembly having a reaming head over the proximal end of the intramedullary reamer such that the reaming head contacts bone. Further, the method includes driving the cannulated reamer into bone to a predetermined depth, thereby forming a central bone pocket. The method further comprising removing the intramedullary reamer and cannulated reamer assembly from the intramedullary canal and central bone pocket. Additionally, there is a step of placing a reaming guide assembly at least partially into the intramedullary canal and central bone pocket. The reaming guide assembly comprises a trial stem, a guide tube assembly, and a handle assembly. The trial stem has a proximal end and is configured to fit into the intramedullary canal. Further, the guide tube assembly has a proximal end and distal end that is rotatably fixed to the proximal end of the trial stem at an oblique angle such that the guide tube assembly at least partially resides in the central bone pocket when the trial stem is fully seated in the intramedullary canal. The handle assembly is fixed at the proximal end of the trial stem such that the handle assembly at least partially resides in the central bone pocket when the trial stem is fully seated in the intramedullary canal. Also included is the step of placing the cannulated reamer assembly over the proximal end of the guide tube assembly such that the reaming head contacts bone at a first position. The method further comprises the step of driving the cannulated reamer into bone to a predetermined depth, thereby forming a first bone cavity adjacent to the central bone pocket.

In one embodiment, the method further comprises the step of rotating the handle assembly and guide tube assembly with respect to the trial stem while partially residing within the central pocket to a second position.

According to another aspect of the invention, the method further comprises the step of reaming bone at the second position with the cannulated reamer assembly placed over the guide tube assembly, thereby forming a second bone cavity adjacent to the central pocket.

BRIEF DESCRIPTION OF THE FIGURES

FIGS. 12A-D show different views of one embodiment of a tibial metaphyseal reconstruction device of the present invention.

DETAILED DESCRIPTION

As used herein, when referring to the surgical reaming instrument of the present invention, the term "proximal" means closer to the surgeon or in a direction toward the surgeon and the term "distal" means more distant from the surgeon or in a direction away from the surgeon. The term "anterior" means towards the front part of the body or the face and the term "posterior" means towards the back of the body. The term "medial" means toward the midline of the body and the term "lateral" means away from the midline of the body.

Figure 1A:
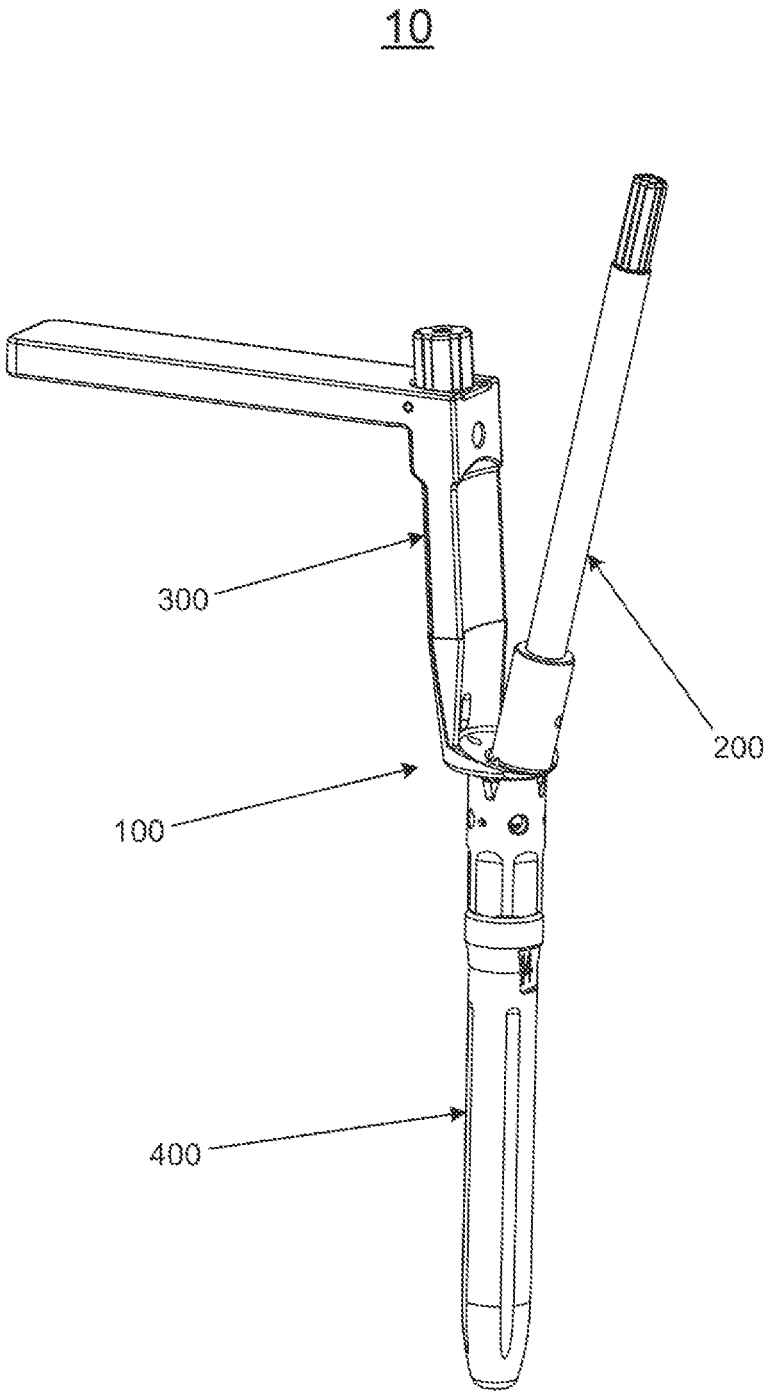
FIG. 1A shows an assembled perspective view of one embodiment of a surgical reaming instrument of the present invention.
Figure 1B:
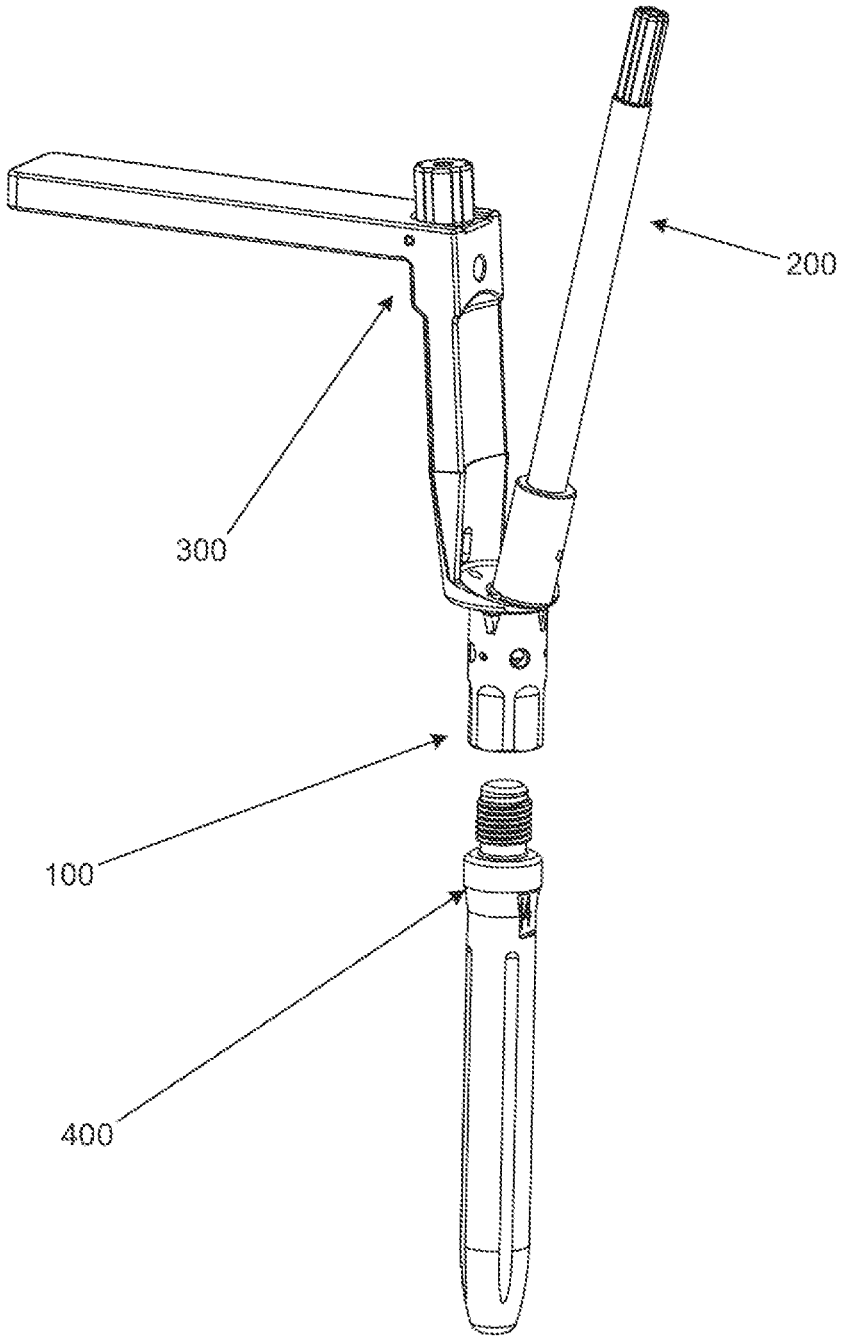
FIG. 1B shows a partially exploded perspective view of the surgical reaming instrument shown in FIG. 1A with a trial stem separated therefrom.

FIG. 1A shows a surgical reaming instrument 10. The surgical reaming instrument 10 generally includes a reaming guide assembly 100, a guide tube assembly 200, a handle assembly 300, and a trial stem 400, each of which will be described in further detail below. FIG. 1B shows the surgical reaming instrument 10 with the trial stem 400 removed from the reaming guide assembly 100.

Figure 2B:
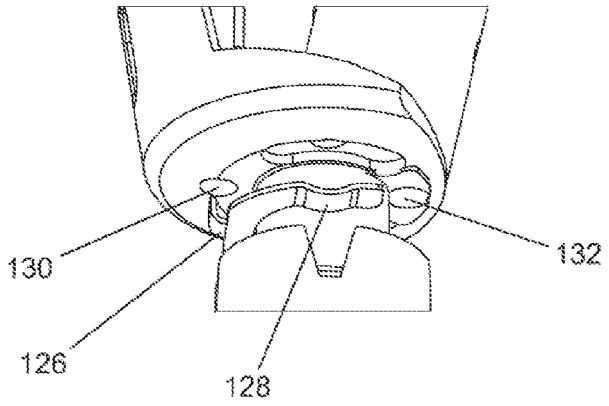
FIG. 2B shows a partially assembled perspective view of a spring detent of the reaming guide shown in FIG. 2A with a spring detent thereof being visible.
Figure 2A:
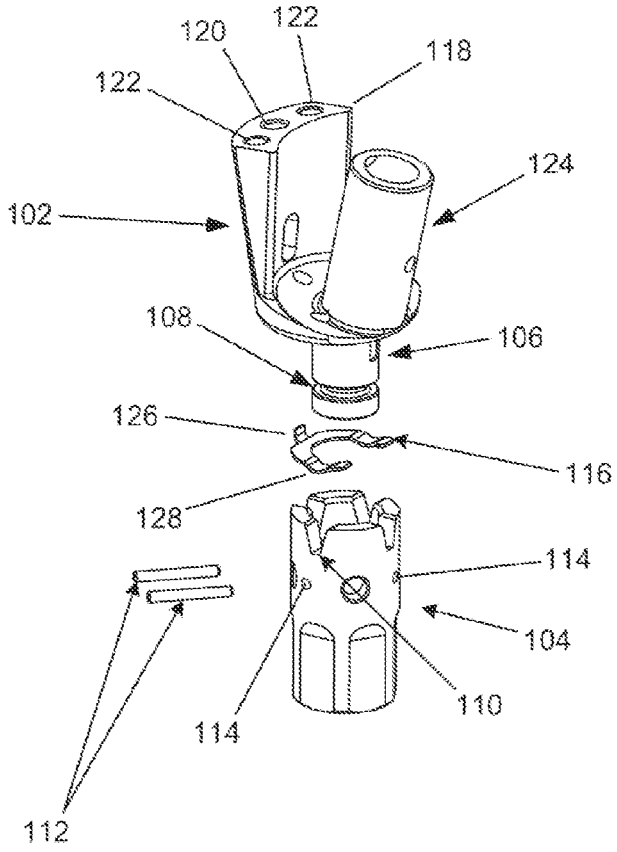
FIG. 2A shows an exploded perspective view of a reaming guide the surgical reaming instrument shown in FIG. 1A.
Figure 2C:
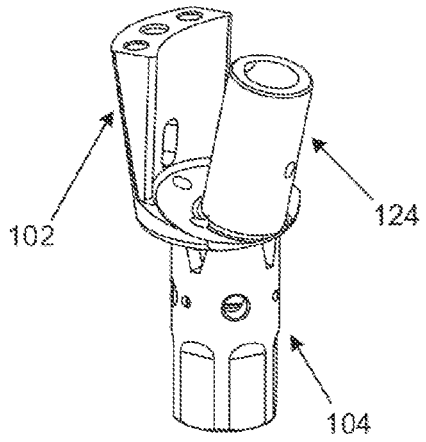
FIG. 2C shows an assembled perspective view of the reaming guide shown in FIG. 2A.

FIGS. 2A-C show the reaming guide assembly 100 in detail. FIG. 2A shows an exploded view of the components of the reaming guide assembly 100. Reaming guide assembly 100 generally includes a reaming guide 102, a reaming guide collar 104, and a spring detent 116. The reaming guide 102 includes a handle receiving portion 118 and a guide tube receiving portion 124. Reaming guide 102 further includes a distally projecting extension 106, which is configured to fit within a hollow proximal portion of the reaming guide collar 104. When the distally projecting extension 106 is within the hollow proximal portion of the reaming guide collar 104, collar apertures 114 align with a notch 108 in the distally projecting extension 106. This allows for reaming guide locking pins 112 to be placed through collar apertures 114 and sit within the notch 108 in the distally projecting extension 106. When the locking pins 112 are in place, the reaming guide 102 and the reaming guide collar 104 are restricted from moving distally or proximally with respect to each other.

FIG. 2B shows a detailed view of spring detent 116 located between partially assembled reaming guide 102 and reaming guide collar 104. Referring to FIGS. 2A-B, spring detent 116 includes ridges 128 and a protrusion 126. Spring detent 116 is generally horseshoe shaped and surrounds a portion of the distally projecting extension 106 proximal to the notch 108 when the distally projecting extension 106 is within the reaming guide collar 104. The spring detent protrusion 126 fits into one of apertures 130, 132 on the underside of the reaming guide 102. Additionally, each ridge 128 in the spring detent 116 sits within a respective collar notch 110 in the reaming guide collar 104. When a surgeon or other operating room personnel inserts the reaming guide 102 into the reaming guide collar 104, the spring detent protrusion 126 preferably engages the aperture 130, for instance, and both the spring detent 116 and reaming guide 102 can be rotated until the ridges 128 engage their respective collar notches 110. When the ridges 128 engage the collar notches 110, this engagement can be felt and feedback is provided to ensure that the reaming guide 102 is in a position such that locking pin aperture 132 is aligned with another of the collar notches 110. FIG. 2C shows the reaming guide assembly 100 when reaming guide 102, reaming guide collar 104 and spring detent 116 are all assembled.

Figure 3B:
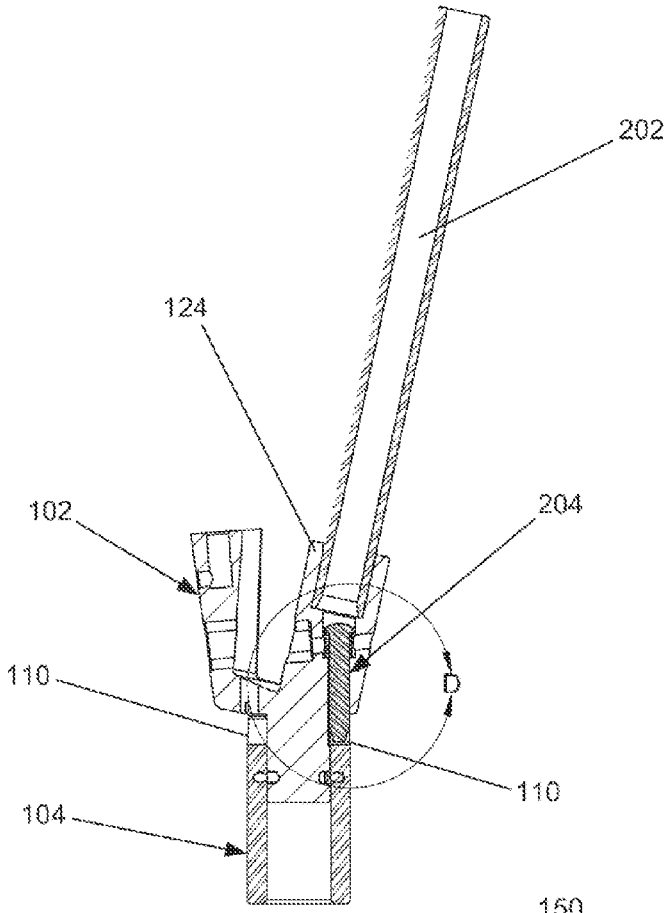
FIG. 3B shows a cross section view of the reaming guide assembly and the guide tube assembly taken along line 3B-3B of FIG. 3A.
Figure 3A:
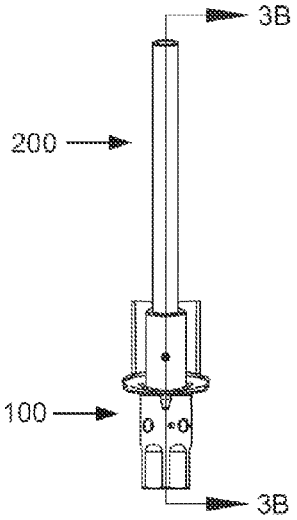
FIG. 3A shows a side view of a reaming guide assembly and a guide tube assembly.
Figure 3C:
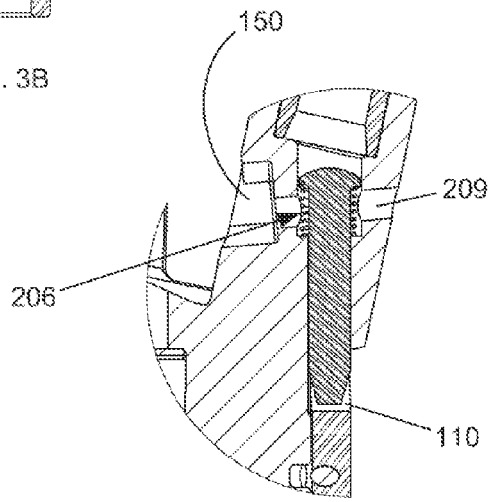
FIG. 3C shows an enlarged view of an attachment mechanism shown in FIG. 3B.

FIGS. 3A-C show detailed views of the guide tube assembly 200 together with the reaming guide assembly 100. FIG. 3A shows a side view of the reaming assembly 100 and the guide tube assembly 200, along with section origin 3B.

FIG. 3B shows a cross section of the reaming guide assembly 100 and guide tube assembly 200 along section origin 3B. FIG. 3C shows an enlarged view of circular section D from FIG. 3B. Referring to FIGS. 3B-C, a locking pin 204 is seated partially within the guide tube receiving portion 124 and further through one of locking pin apertures 130, 132. The locking pin 204 is surrounded by a coil spring 206 dimensioned such that the head of locking pin 204 cannot pass through coil spring 206, and coil spring 206 cannot pass through locking pin aperture 132. The coil spring 206 and locking pin 204 are further dimensioned so that when the head of locking pin 204 is resting on the coil spring 206 with no additional force applied, the distal end of the locking pin 204 does not enter any portion of a collar notch 110. Although in FIGS. 3B-C there is no force being applied to the locking pin 204 other than the weight of the locking pin 204 itself, the locking pin 204 is shown in the locked position for purposes of illustration (i.e. the distal end of the locking pin 204 is within a collar notch 110). The locking pin 204, when in the locked position, prevents relative rotation between the reaming guide 102 and the reaming guide collar 104 since the locking pin 204 rests in one of collar notches 110 of reaming guide collar 104.

Guide tube receiving portion 124 of the reaming guide 102 may include one or more rinse holes 209 to improve the ability to clean the surgical reaming instrument 10. Once the locking pin 204 is seated within the guide tube receiving portion 124 and further through locking pin aperture 132, a guide tube 202 may be inserted into the guide tube receiving portion 124. The guide tube 202 may be permanently fixed within the guide tube receiving portion 124, for example, by welding. As will be explained in more detail below, guide tube 202 is used to act as a guide for a cannulated reamer assembly 600 when reaming a bone.

Figure 4A:
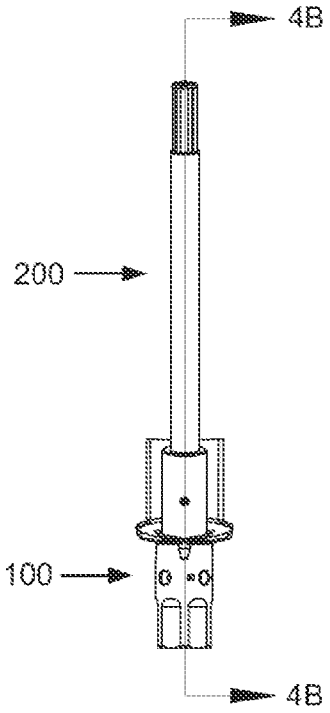
FIG. 4A shows a side view of a reaming guide assembly and a guide tube assembly with a locking rod.
Figure 4B:
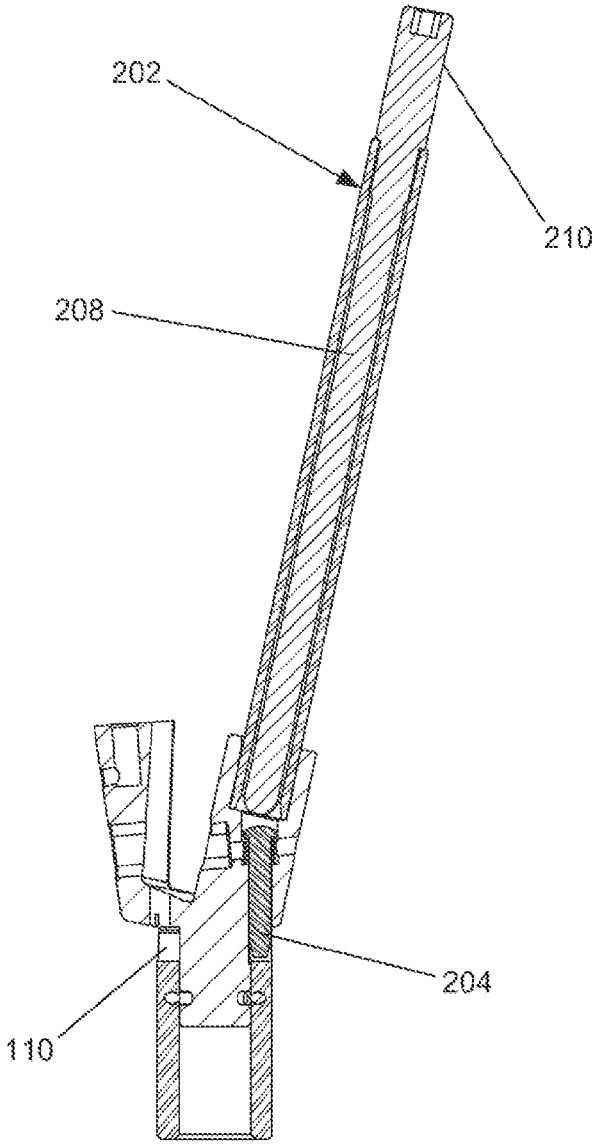
FIG. 4B shows a cross section view of the reaming guide assembly and the guide tube assembly with locking rod taken along line 4B-4B of FIG. 4A.

FIGS. 4A-4B show detailed views of the guide tube assembly 200 and the reaming guide assembly 100 with locking rod 208 inserted into guide tube 202. FIG. 4A shows a side view of the reaming assembly 100 and the guide tube assembly 200, along with section origin 4B. FIG. 4B shows a cross section of the reaming guide assembly 100 and guide tube assembly 200 along section origin 4B. Locking rod 208 is inserted into guide tube 202 and can be fixed, for example, by threading the locking rod 208 into corresponding threads on the inside of guide tube 202. When the locking rod 208 is fully or nearly fully inserted into the guide tube 202, a proximal portion of the locking rod 208 clears the guide tube 202 and provides a handle 210 for the surgeon to manipulate reaming guide 102. By rotating the locking rod handle 210, and thus the locking rod 208, the distal end of the locking rod 208 makes contact with, and applies force to, the head of the locking pin 204. This rotation can be continued until the locking pin 204 is fully driven into a collar notch 110. Once fully driven into the collar notch 110, the system is in the locked position and the reaming guide 102 is prevented from rotating relative to the reaming guide collar 104.

Figure 5A:
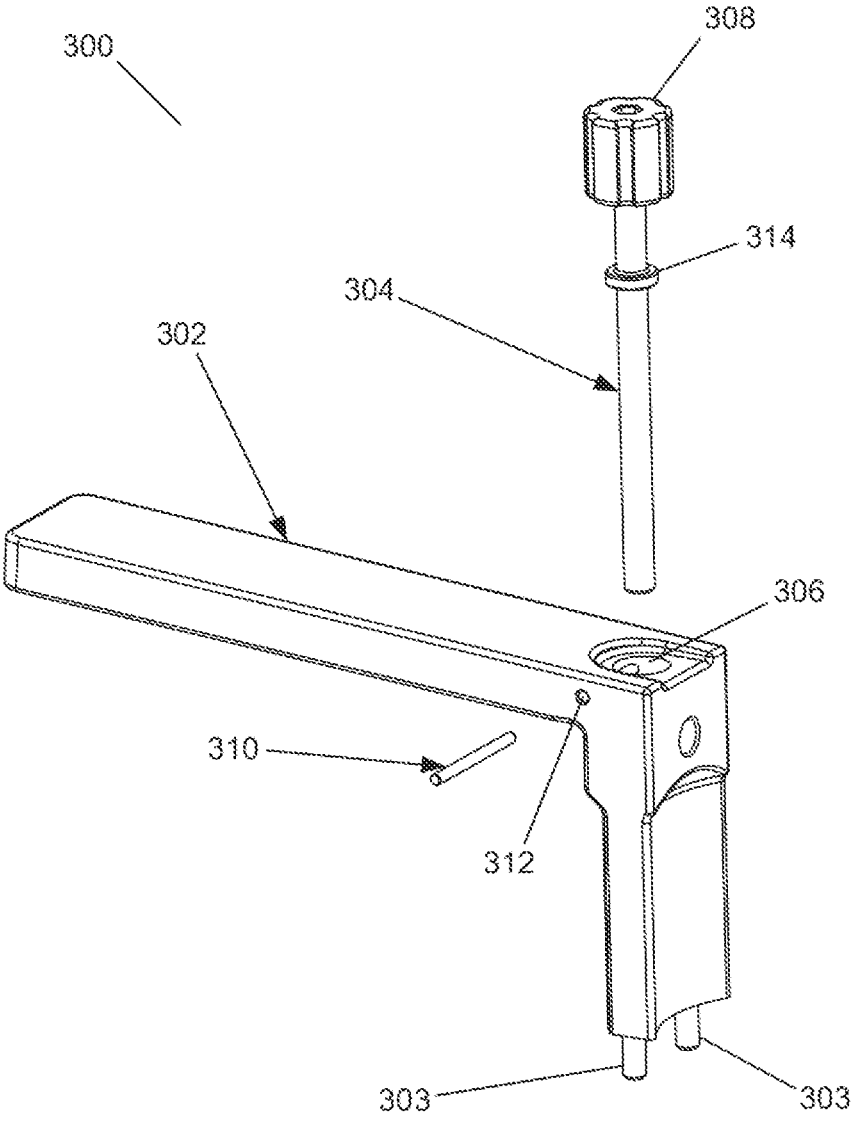
FIG. 5A shows an exploded perspective view of a handle assembly of one embodiment of the surgical reaming instrument of the present invention.
Figure 5C:
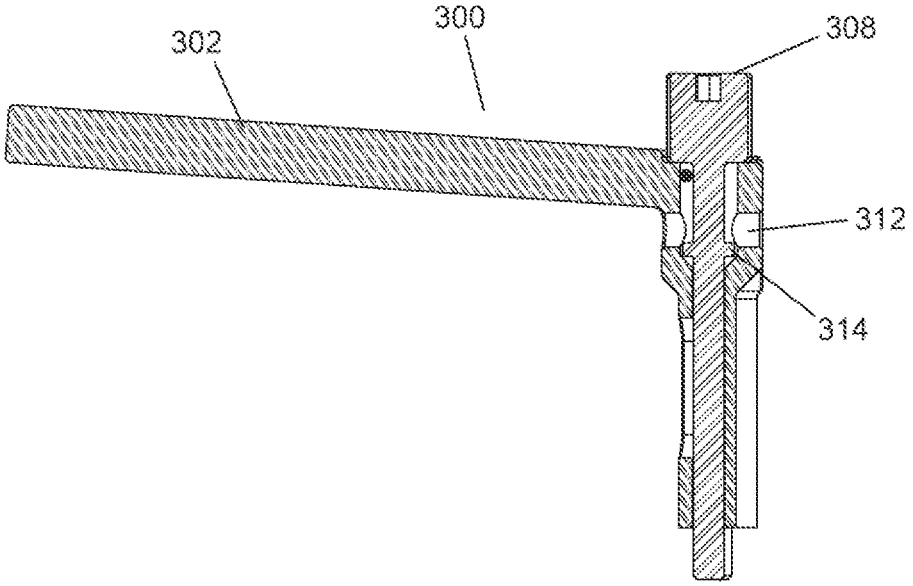
FIG. 5C shows a cross section view of the handle assembly taken along line 5C-5C of FIG. 5B.
Figure 5B:
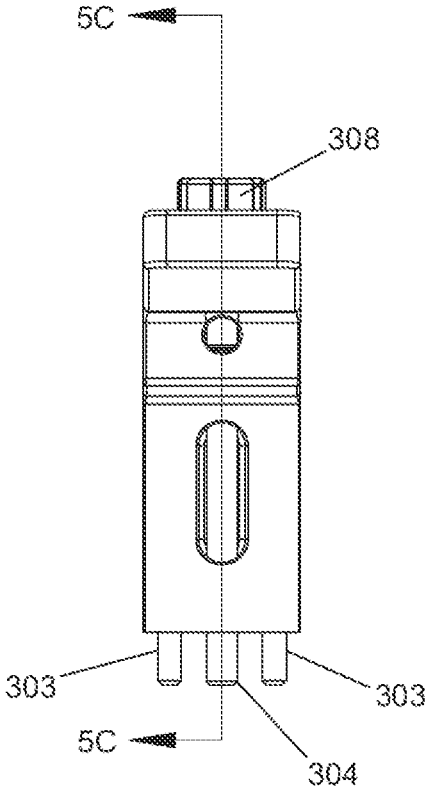
FIG. 5B shows a side view of the handle assembly of FIG. 5A.
Figure 5D:
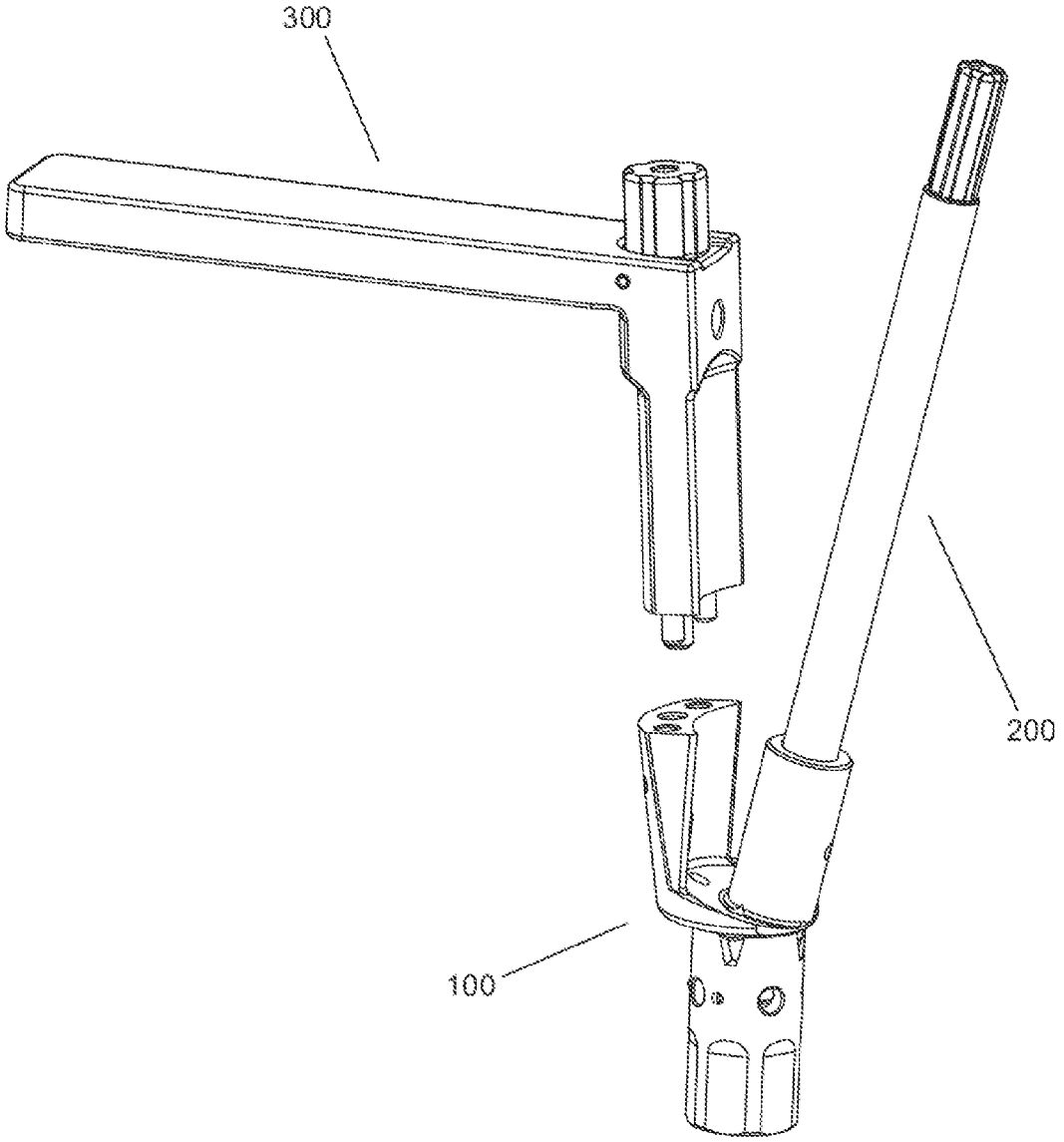
FIG. 5D shows a perspective view of a handle assembly detached from a guide body assembly and guide tube assembly.

FIG. 5A shows an exploded view of the handle assembly 300. FIG. 5B shows a side view of the handle assembly 300 with section origin 5C. FIG. 5C shows a cross section of the handle assembly 300 along section origin 5C. FIG. 5D shows the handle assembly 300 fully assembled and exploded from the remainder of the surgical reaming instrument 10. Referring now to FIGS. 5A-D, handle assembly 300 generally includes a handle 302, to allow the surgeon to grip the surgical reaming instrument 10, and an attachment screw 304, to attach the handle assembly 300 to the reaming guide 102. Alignment pins 303 are inserted into their respective flanking apertures 122 of the handle receiving portion 118 of the reaming guide 102. These alignment pins 303 align the screw aperture 306 of the handle assembly 300 with the center aperture 120 of the handle receiving portion 118 of the reaming guide 102. Once aligned, the surgeon can insert the attachment screw 304 into the screw aperture 306 and further into the center aperture 120 by gripping and rotating the screw handle 308 so that the attachment screw 304 threads fully through the screw aperture 306. Once the attachment screw 306 is fully inserted into the screw aperture 306, the screw collar 315 sits distal to the retaining pin aperture 312. At this point, the surgeon can insert the screw retaining pin 310 into the retaining pin aperture 312 such that the screw retaining pin 310 sits proximal the screw collar 314. This ensures that the attachment screw 304 is locked into place and cannot exit the screw aperture 306.

Figure 6A:
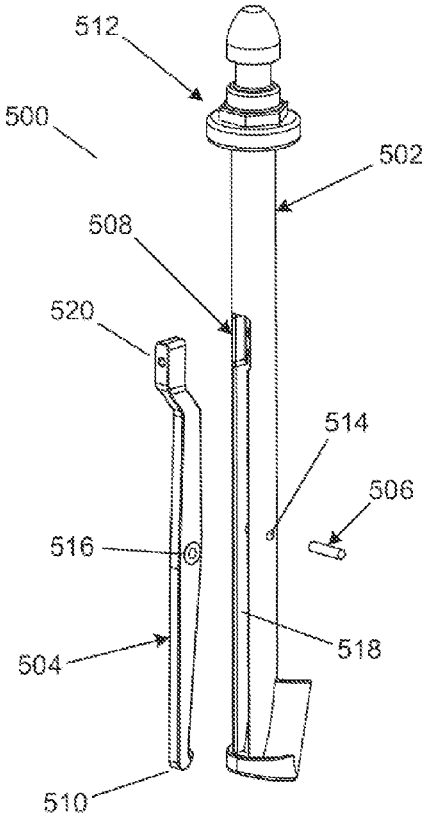
FIG. 6A shows an exploded perspective view of an insertion/removal tool for use with a surgical reaming instrument.
Figure 6B:
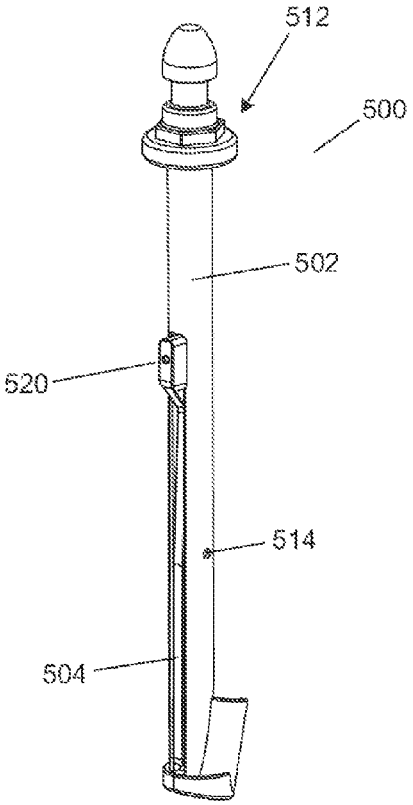
FIG. 6B shows a perspective view of an assembled insertion/removal tool for use with a surgical reaming instrument.

FIG. 6A shows an exploded view of an optional insertion/removal tool 500. FIG. 6B shows a view of the assembled insertion/removal tool 500. The insertion/removal tool 500 is optionally used to insert or remove the surgical reaming instrument 10. Referring to FIGS. 6A-B, an insertion/removal tool 500 generally includes a tool body 502 and a locking lever 504. Tool body 502 includes a slot 518 into which the locking lever 504 is installed. Locking lever 504 includes an aperture 516 that aligns with pivot pin apertures 514 on each side of the tool body 502. Pivot pin 506 can be inserted through locking lever aperture 516 and both pivot pin apertures 514 on the tool body 502. The pivot pin 506 allows the locking lever 504 to pivot about the pivot pin 506. Additionally, the proximal end of the body slot 518 includes a preload spring 508. The preload spring 508 contacts the locking lever actuator 520. When the locking lever actuator 520 is pressed, the preload spring 508 compresses and the locking lever 504 pivots about pivot pin 506, ultimately causing the lever hook 510 to move away form the body 502 of the insertion/removal tool 500. The end of the tool 512 may optionally be configured to match a universal instrument handle.

Figure 6C:
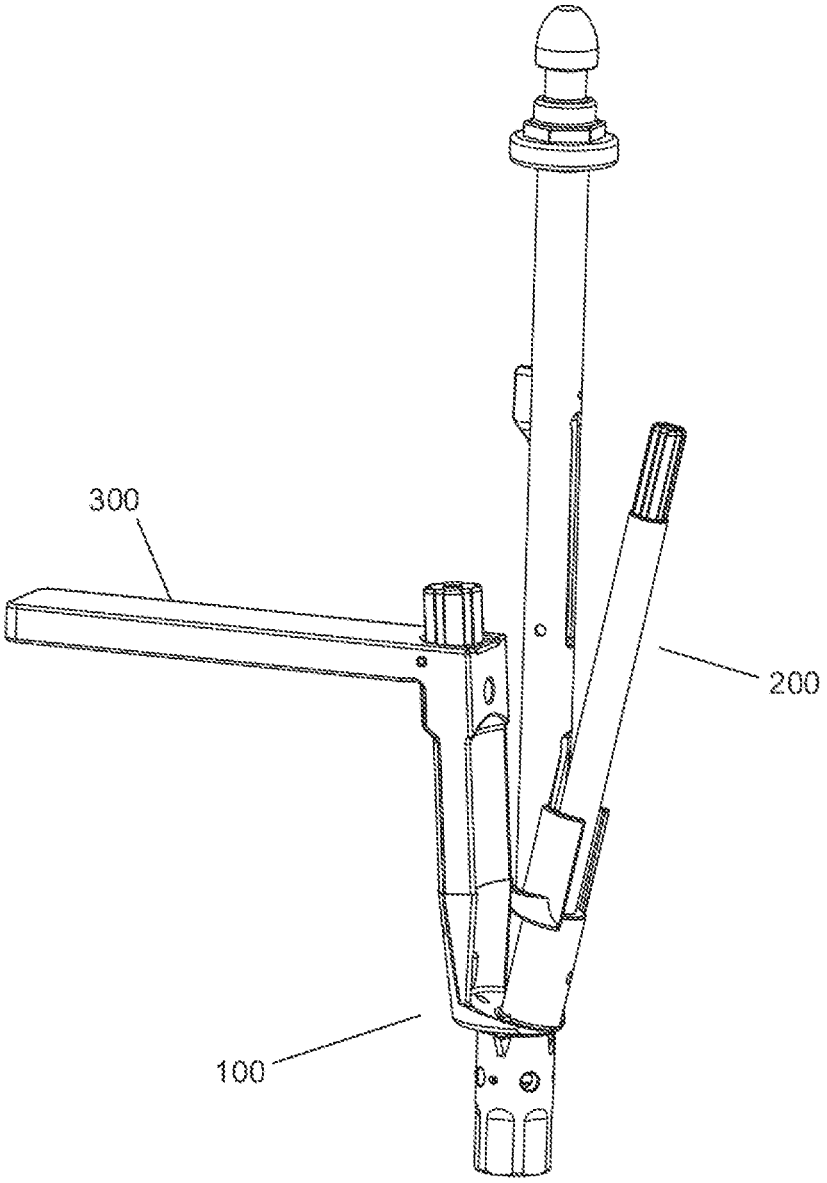
FIG. 6C shows a perspective view of an insertion/removal tool connected to a surgical reaming instrument.
Figure 6D:
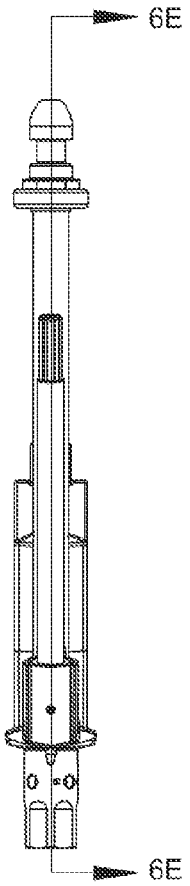
FIG. 6D shows a side view of an insertion/removal tool connected to a surgical reaming instrument.
Figure 6E:
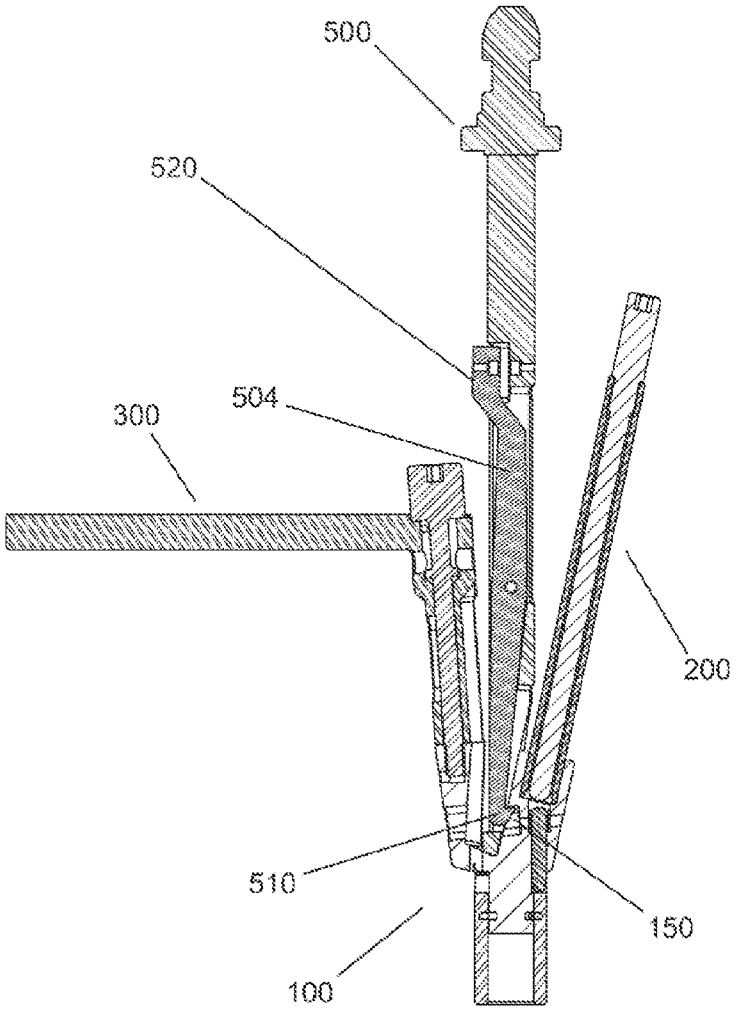
FIG. 6E shows a cross section view of an insertion/removal tool connected to a surgical reaming instrument taken along line 6E-6E of FIG. 6D.

FIG. 6C shows the insertion/removal tool 500 assembled with the reaming guide assembly 100, the guide tube assembly 200, and the handle assembly 300. FIG. 6D shows a side view of the illustration in FIG. 6C along with section origin 6E. FIG. 6E shows a cross section view of the illustration in FIG. 6D along section origin 6E. Referring to FIGS. 6C-E, the insertion/removal tool 500 can be slid distally toward the guide body receiving portion 124 of the reaming guide assembly 100 until the lever hook 510 snaps into a hook receiving portion 150 of the guide body receiving portion 124 of the reaming guide assembly 100. The preload spring 508 provides enough force on the proximal end of the locking lever 504 to keep the insertion/removal tool 500 engaged with the reaming guide assembly 100. If a surgeon, for instance, desires to detach the insertion/removal tool 500 from the reaming guide assembly 100, he simply applies pressure to the locking lever actuator 520 such that the locking lever 504 pivots about pivot pin 506 and the lever hook 510 disengaged from the reaming guide assembly 100.

Figure 7A:
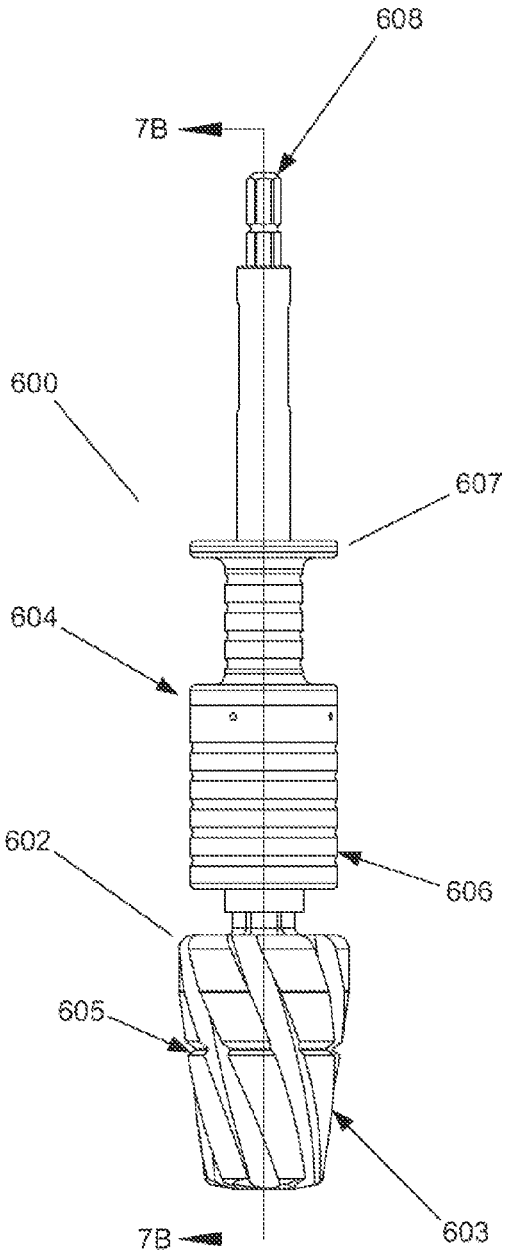
FIG. 7A shows a side view of a cannulated reamer assembly.

FIG. 7A shows a side view of a cannulated reamer assembly 600 with section origin 7B. Cannulated reamer assembly 600 generally includes reaming head 602 and reamer shaft assembly 604. Reamer shaft assembly includes quick connect mechanism 606, shaft handle 607 and drill attachment end 608. The surgeon can grip the quick connect mechanism 606 and insert the reaming head 602 into the distal end of the reamer shaft assembly 604 to connect the reaming head 602 to the reamer shaft assembly 604. To disconnect the reaming head 602 from the reamer shaft assembly 604, the surgeon can grip the shaft handle 607 and pull the reamer shaft assembly 604 proximally away from the reaming head 602. The reamer shaft assembly 604 further includes a drill attachment end 608 on the proximal end of the reamer shaft assembly 604. The drill attachment end 608 can be attached to a drill, such as an electric or pneumatic drill, in order to drive the cannulated reamer assembly 600. Reaming head 602 may include a depth indicator 605, such as a groove in the reaming head 602, that gives feedback to the surgeon, such as visual feedback, to notify the surgeon that the reaming head 602 has traveled a predetermined distance. Reaming head 602 can also contain a tapered distal end 603.

Figure 7B:
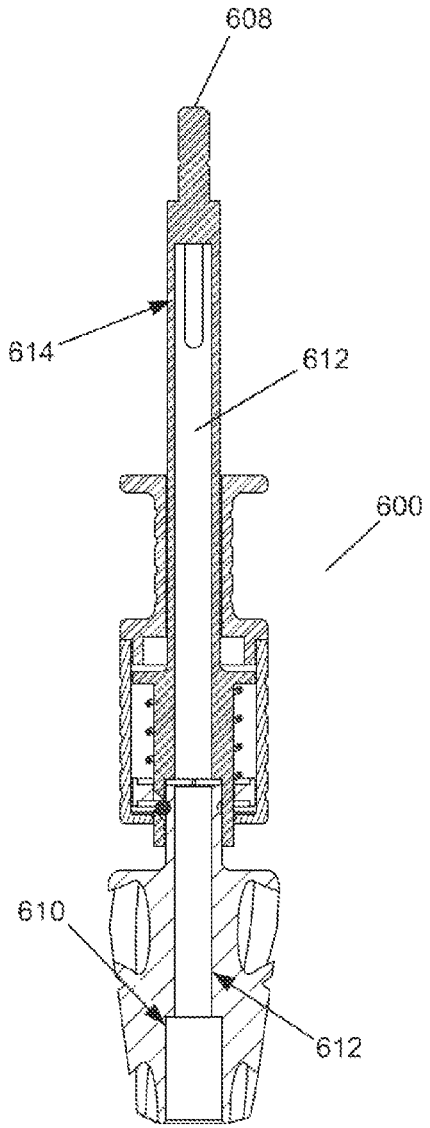
FIG. 7B shows a cross section view of a cannulated reamer assembly taken along line 7B-7B of FIG. 7A.
Figure 7C:
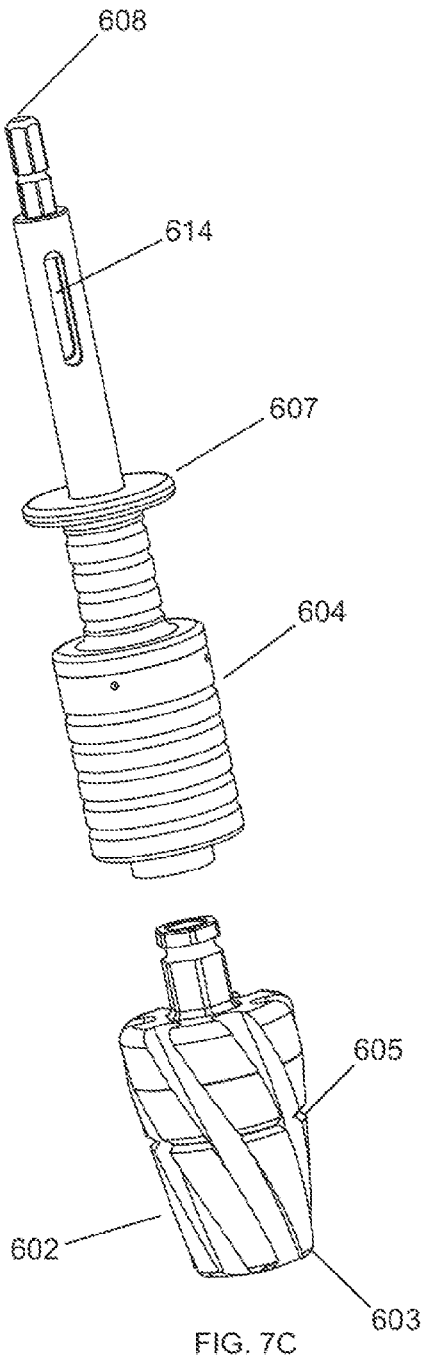
FIG. 7C shows an exploded perspective view of one embodiment of a cannulated reamer assembly of the present invention.
Figure 7D:
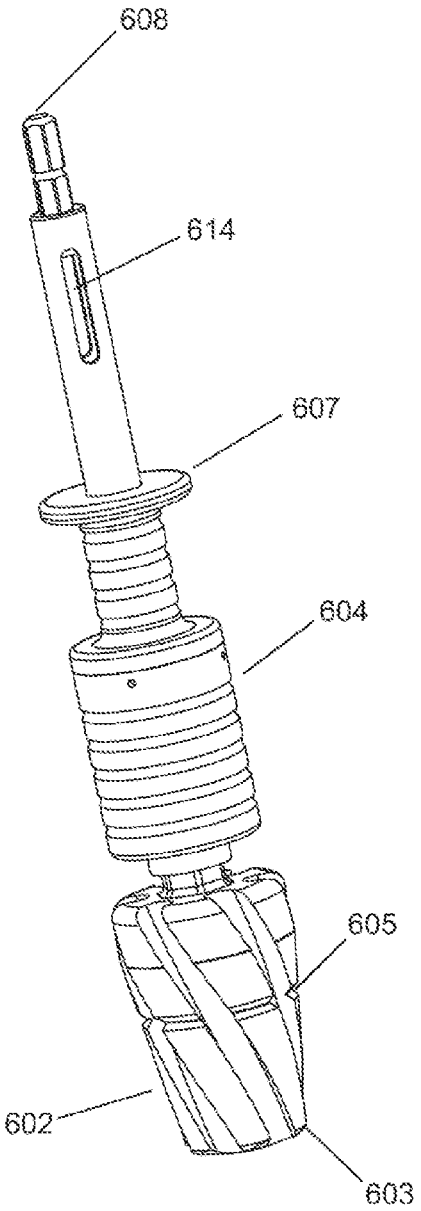
FIG. 7D shows an assembled perspective view of the cannulated reamer assembly of FIG. 7C.

FIG. 7B shows a cross section of the cannulated reamer assembly 600 along the section origin 7B. Reaming head 602 and reamer shaft assembly 604 both include cannulations 612 that allow the cannulated reamer assembly 600 to slide over a rod, such as the guide tube 202 of the guide tube assembly 200 or over the rod of a traditional intramedullary (IM) reamer. The reaming head 602 also includes a counterbore 610 to allow the reaming head 602 to clear the guide tube receiving portion 124 of the reaming guide assembly 100. Additionally, the reamer shaft assembly 604 may include a viewing port 614 located at the proximal end of the cannulation 612 to give the surgeon visual feedback regarding whether or not the cannulated reamer assembly 600 has "bottomed out." Essentially, as long as the rod over which the cannulated reamer assembly 600 is placed cannot be seen through the view port 614, there is no danger of "bottoming out." Once the rod can be seen through the view port 614, the surgeon, for instance, can view whether the cannulated reamer assembly 600 is close to travelling the full distance of which it is capable before the rod makes contact with the proximal closed end of the cannulation 612 of the reamer shaft assembly 604. FIG. 7C shows an exploded view of the cannulated reamer assembly 604 with the reaming head 602 separated from the reamer shaft assembly 604. FIG. 7D shows the cannulated reamer assembly 604 fully assembled.

Figure 8A:
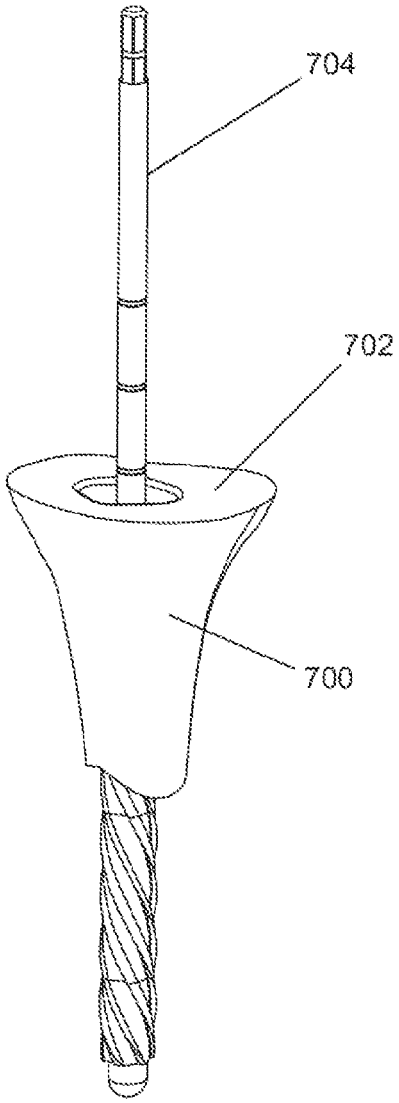
FIG. 8A shows a perspective view of a preparatory reaming step in a tibial bone.
Figure 8C:
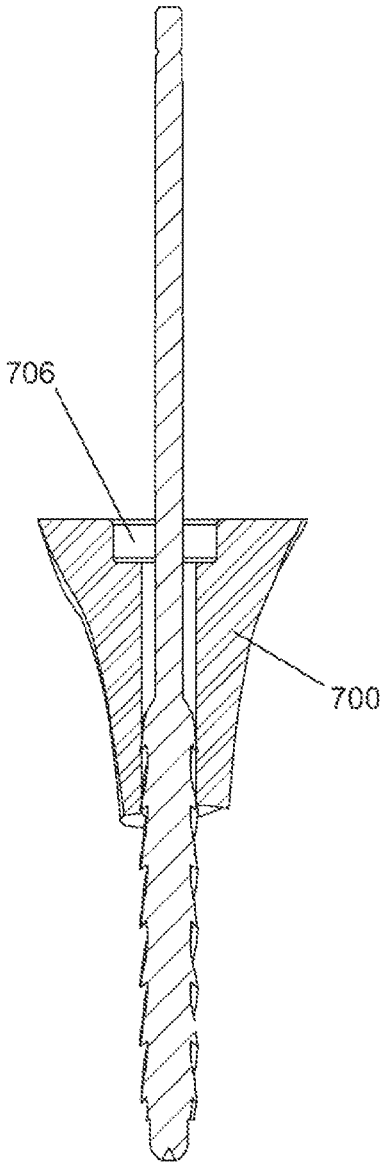
FIG. 8C shows a cross section view of the preparatory reaming step in a tibial bone taken along line 8C-8C of FIG. 8B.
Figure 8B:
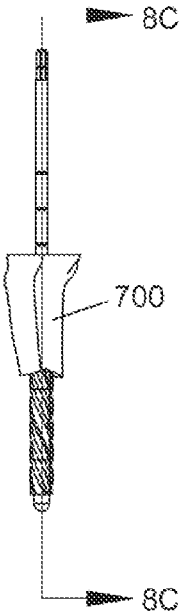
FIG. 8B shows a side view of a preparatory reaming step in a tibial bone.

An example of one method of use of the invention will now be described. Referring now to FIGS. 8A-C, the beginning of one method of a revision procedure is shown. For example, in a revision procedure of a total knee replacement surgery, the initial step is to ream the bone 700 generally along the IM canal. Although the IM reamer 704 is illustrated here as distally reaming the tibia beginning at the tibial plateau 702, this is merely an example. The IM reamer 704 could also proximally ream the femur beginning at the distal end of the femur in substantially the same manner. FIG. 8B shows the initial step along with section origin 14C, and FIG. 8C shows a cross section of the initial step along section origin 14C. As can be seen, the IM reamer 704 enters through the initial bone void 706 that was originally created during a previous knee replacement surgery, for example.

Figure 9A:
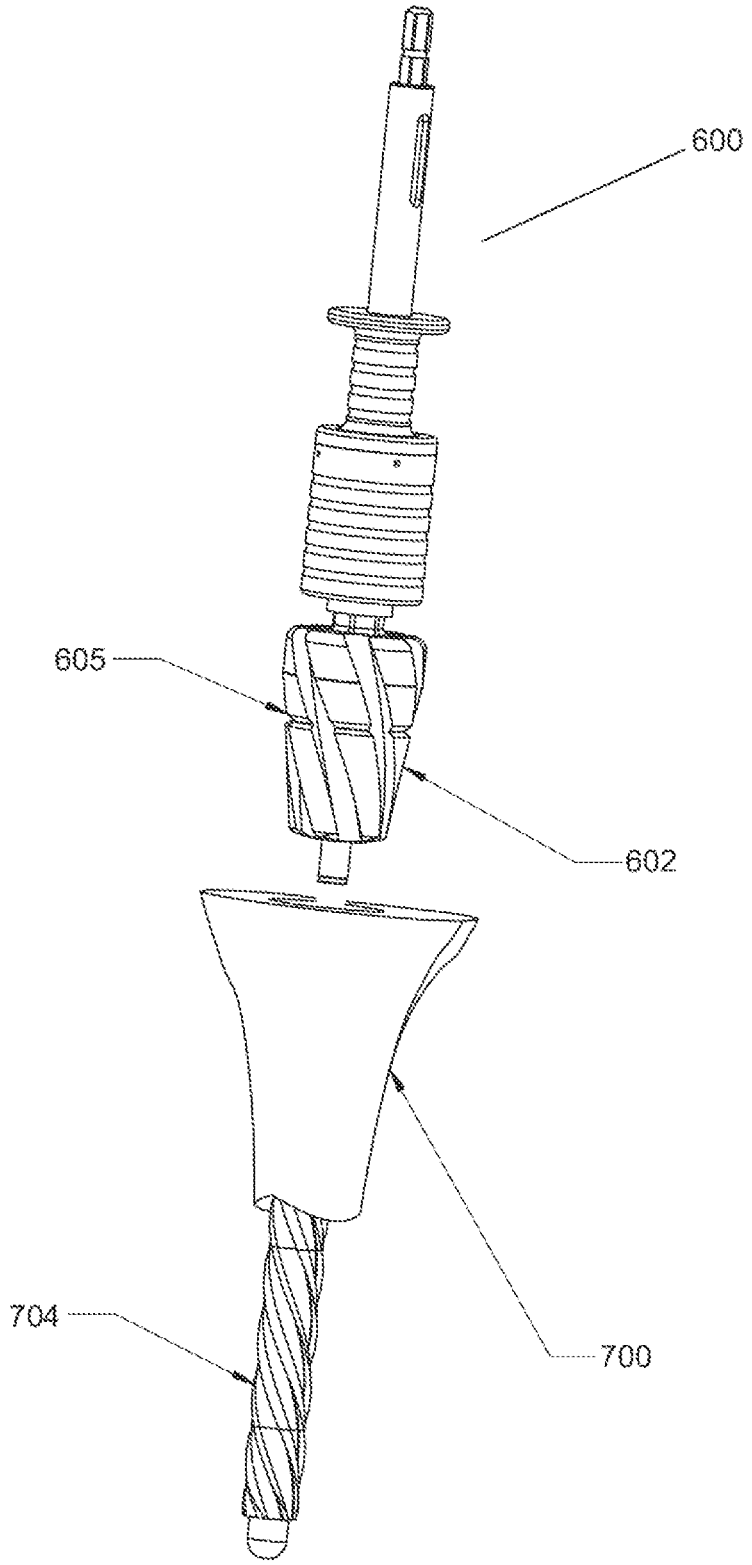
FIG. 9A shows a perspective view of a first reaming step in a tibial bone using a cannulated reamer assembly.
Figure 9B:
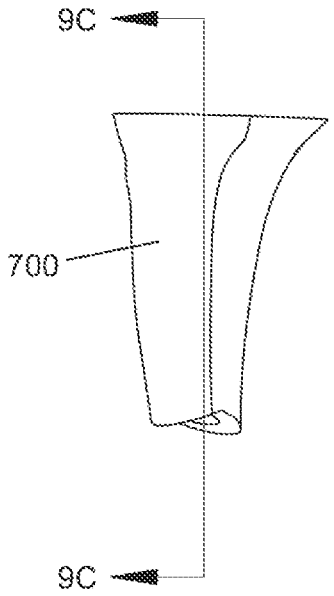
FIG. 9B shows a side view of a tibial bone after a first reaming step has been completed.
Figure 9C:
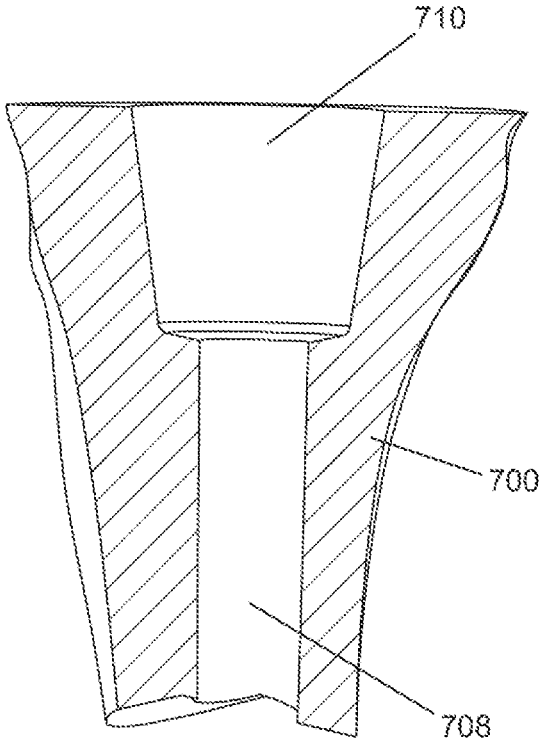
FIG. 9C shows a cross section view of a tibial bone after a first reaming step has been completed with a cannulated reaming assembly taken along line 9C-9C of FIG. 9B.

FIG. 9A shows the first step following the initial tibial or femoral IM canal preparation. The IM reamer 704 used to initially prepare the IM canal is left in place and the cannulation 612 of the cannulated reaming assembly 600 is placed over the proximal end of the IM reamer 704. The surgeon then reams over the stem of the IM reamer 704 using the cannulated reaming assembly 600. The reaming head 602 is driven distally into the tibial bone until the surgeon, optionally using the depth indicator 605 as a guide, determines that the proper depth has been reached based on the dimensions of a MRD to be implanted into the bone. FIG. 9B shows a side view of the bone 700 after this reaming step has been performed, along with section origin 9C. FIG. 9C shows a cross section of the bone following this reaming step along section origin 9C. As can be seen, one void space in the bone 700 is the generally cylindrical preparatory IM reaming void 708 created by the initial preparation step with the IM reamer 704. A central pocket 710 created in the initial reaming step corresponds in shape to the tapered distal end 603 of the reaming head 602.

Figure 10A:
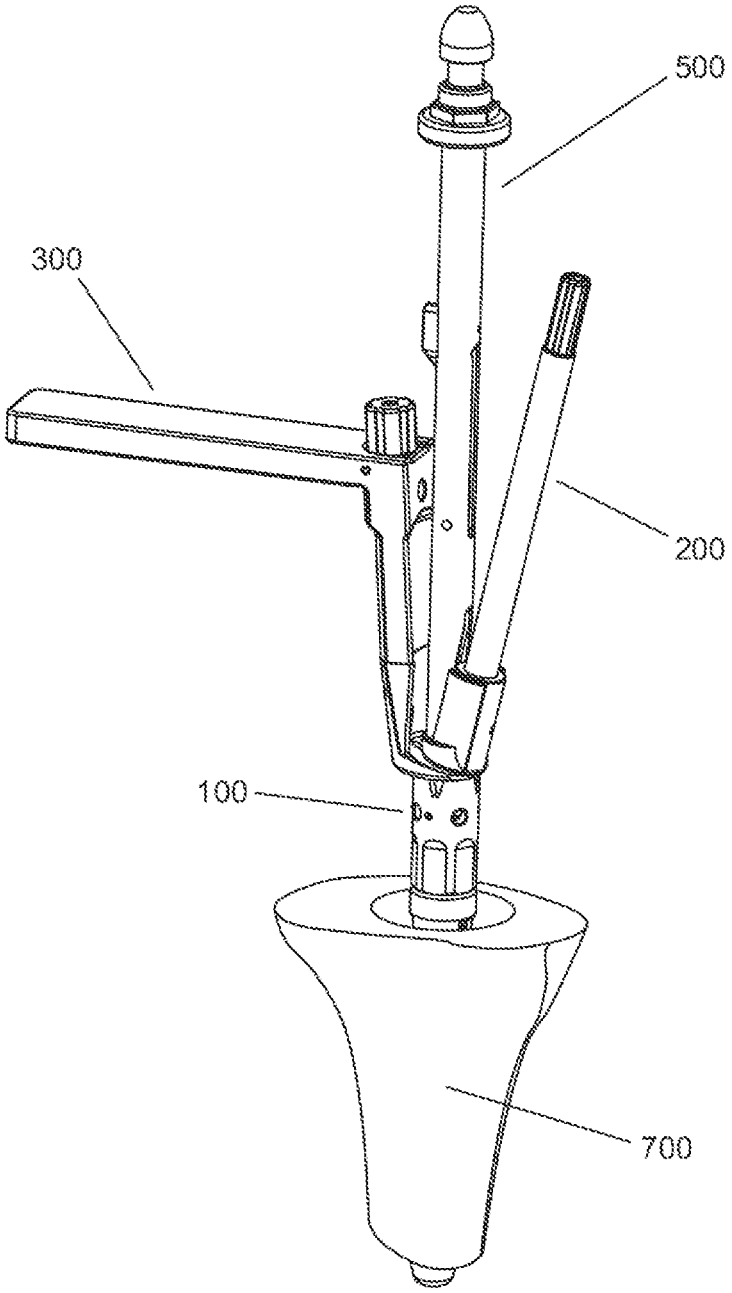
FIG. 10A shows a perspective view of a surgical reaming instrument and tibial bone being prepared for a second reaming step.
Figure 10B:
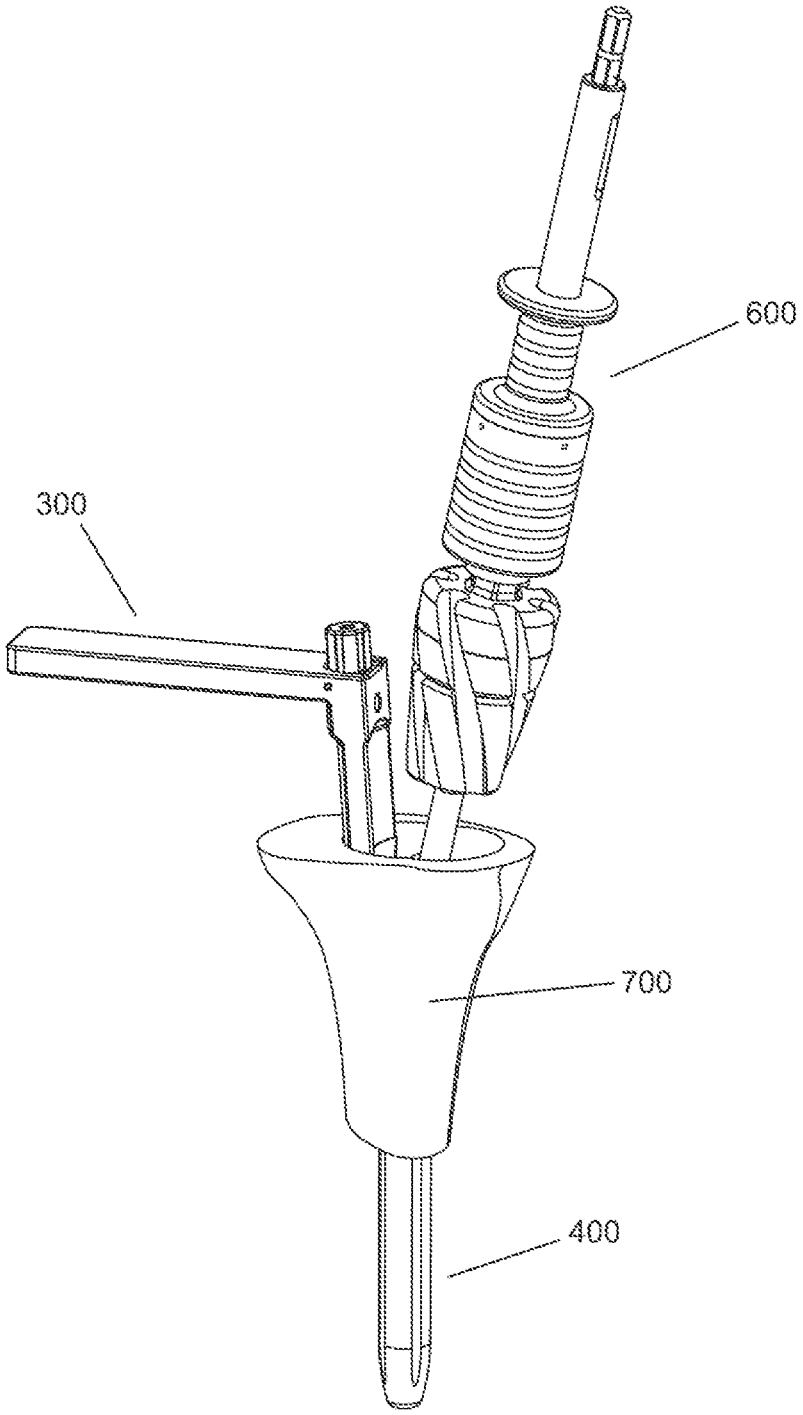
FIG. 10B shows a perspective view of a surgical reaming instrument and tibial bone after the second reaming step has been completed.
Figure 10D:
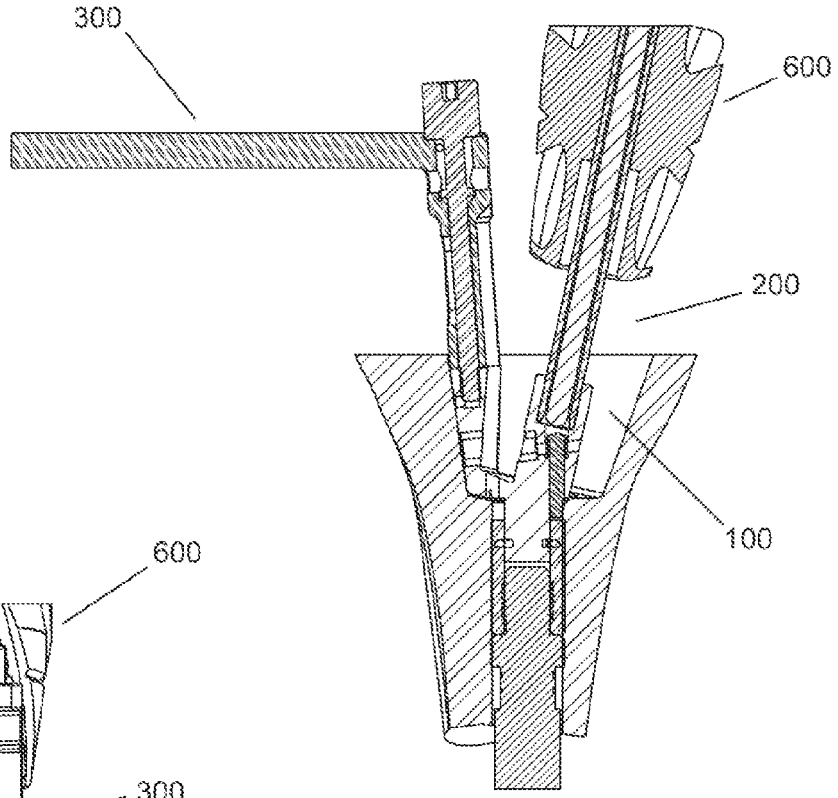
FIG. 10D shows a cross section view of a surgical reaming instrument and tibial bone after the second reaming step has been completed taken along line 10D-10D of FIG. 10C.
Figure 10C:
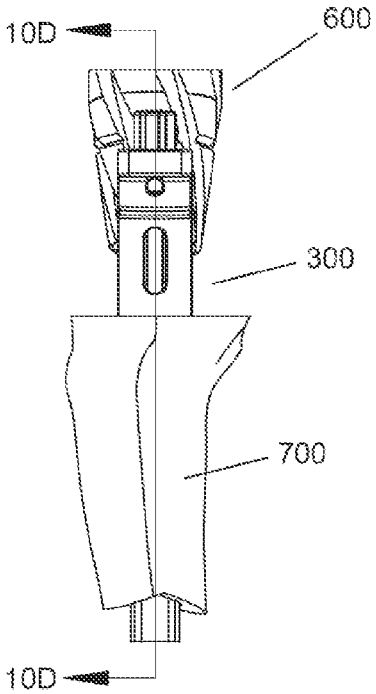
FIG. 10C shows a side view of a surgical reaming instrument and tibial bone after the second reaming step has been completed.

FIG. 10A shows the reaming guide setup for the second reaming step. The cannulated reaming assembly 600 first is removed from the IM reamer 704. Then, the fully assembled reaming guide assembly 100, guide tube assembly 200, handle assembly 300, and optional insertion/removal tool 500 are placed near bone 700. FIG. 10B shows the surgical reaming instrument 10 inserted in the central pocket 710 in the bone after the second reaming step has been completed. FIG. 10C shows a side view of FIG. 10B along with section origin 10D. FIG. 10D shows a cross section of FIG. 10C along section origin 10D. Once inserted, as seen in FIG. 10D, the reaming guide 102 makes contact with a portion of the bone 700 surrounding central pocket 710. The cannulated reaming assembly 600 is then preferably inserted over the guide tube 202 of the guide tube assembly 200. The surgeon may use the handle 302 of the handle assembly 300 for optimum angular positioning of the reaming guide 102. The reaming head 602 of the reaming assembly 600 is then driven, either manually or with a drill, distally along the guide tube 202 to ream the bone 700. The reaming guide assembly 100 acts as a depth stop to ensure that reaming head 602 can only travel a predetermined distance. Although the counterbore 610 of the reaming head 602 will pass over the guide tube receiving portion 124 of the reaming guide assembly 100, the remainder of the reaming guide assembly 100 will act as a stop for the distal end of the reaming head 602.

Figure 11A:
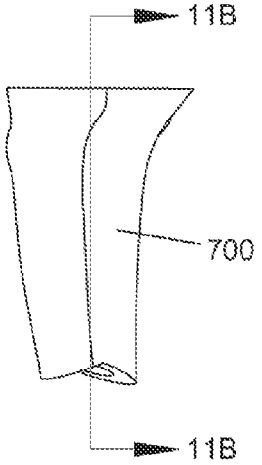
FIG. 11A shows a side view of a tibial bone after the second reaming step has been completed.
Figure 11B:
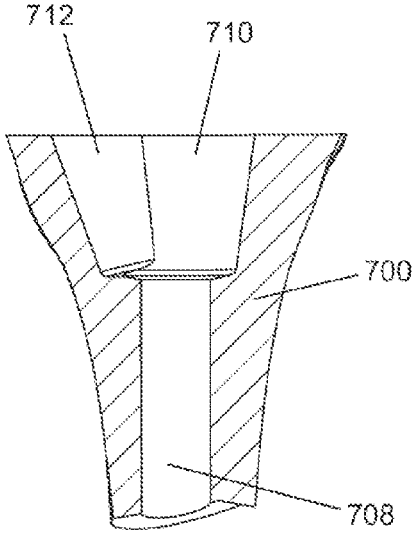
FIG. 11B shows a cross section view of a tibial bone after the second reaming step has been completed taken along line 11B-11B of FIG. 11A.
Figure 11C:
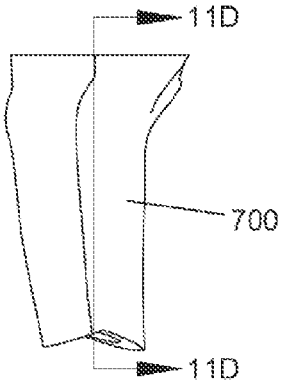
FIG. 11C shows a side view of a tibial bone after the third reaming step has been completed.
Figure 11D:
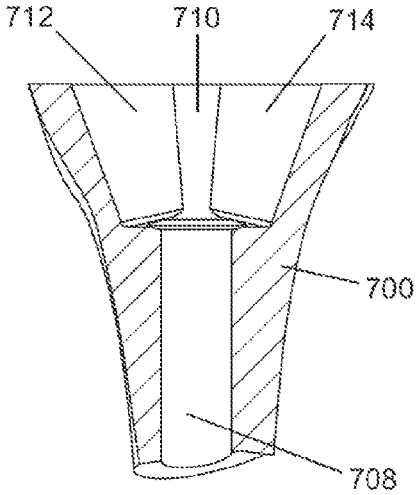
FIG. 11D shows a cross section view of a tibial bone after the third reaming step has been completed taken along lien 11-D-11D of FIG. 11C.
Figure 11E:
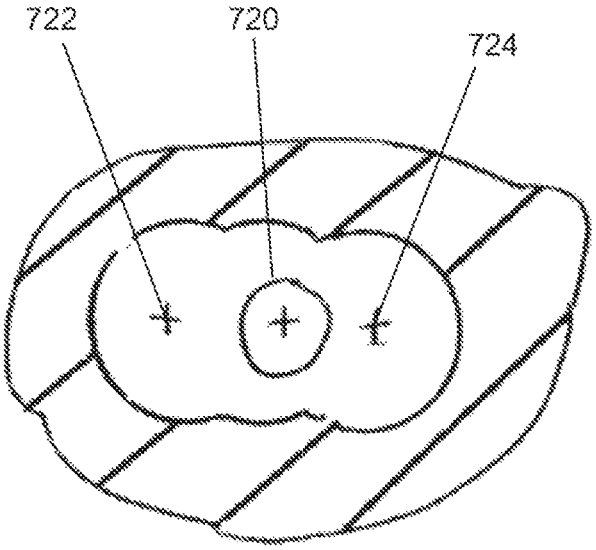
FIG. 11E shows a top view of a tibial bone after the third reaming step has been completed.

FIG. 11A shows a side view of the bone 700 after the second reaming step is completed, along with section origin 11B. FIG. 11B shows a cross section of the bone 700 along section origin 11B. In addition to the central pocket 710, a medial reaming void 712 preferably exists along the path taken by the reaming head 602 in the second reaming step. If necessary, depending on the size and the shape of the bone void, a third reaming step can be undertaken. With the surgical reaming instrument 10 in the bone void, the reaming head 602 is moved proximally along the guide tube 202 until it clears the bone 700. The locking rod handle 210 of the locking rod 208 is preferably rotated to release the force on the locking pin 204. The coil spring 206 will cause the locking pin 204 to move proximally and clear that collar notch 110. Once the locking pin 204 clears the collar notch 110, the system is in what may be referred to as an unlocked position and the reaming guide 102 can rotate in relation to the reaming guide collar 104. One in the unlocked position, the surgeon can use the handle 302 to rotate the reaming guide 102 into the desired position for a further reaming step. Angular stops may be provided in the handle 302 so that angular rotation between reaming steps can be accurately controlled. Once in place, the locking rod 208 is manipulated to force the locking pin 204 back into the locking position so that the third reaming step can be performed. The third reaming step is preferably completed in substantially the same manner as the second reaming step, with the only difference being the portion of the bone 700 being reamed. FIG. 11C shows a side view of the bone 700 after the third reaming step has been performed, along with section origin 11D. FIG. 11D shows a cross section of the bone 700 along section origin 11D after the third reaming step has been performed. As can be seen, in addition to central pocket 710 and medial reaming void 712, there is now a lateral reaming void 714 created as a result of the third reaming step. FIG. 11E shows a top view of bone 700 after the third reaming step. The IM axis 720 corresponds to the center of the central pocket 710 and preparatory IM reaming void 708. The medial reaming axis 722 corresponds to the center of the medial reaming void 712, and the lateral reaming axis 724 corresponds to the center of the lateral reaming void 714. When the reaming is complete, the bone 700 is ready to receive a void filler prosthetic component, such as an MRD, for example. In certain embodiments, the three aforementioned reaming steps do not have to be performed in any particular order, and in other embodiments, not all three of the reaming steps are performed.

Figure 12D:
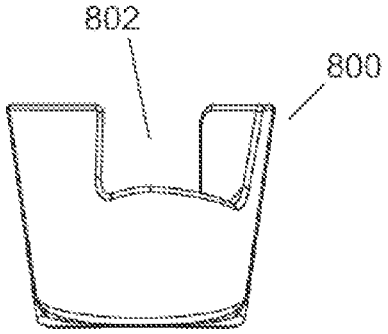

FIGS. 12A-D show different views of a MRD. In this illustrative embodiment, the MRD is a tibial MRD *or tibial void filler* 800. The tibial MRD 800 is placed within the one or more reaming voids 710, 712 and 714 in the bone 700. The tibial MRD 800 includes a *central body 810 and lateral and medial members 812, 814. Tibial MRD 800 also includes a* central opening 802 *that extends through central body 810* to allow insertion of a trial stem 400, in this case a tibial stem. The central opening 802 also allows for insertion of the stem boss of a tibial baseplate (not shown), the tibial baseplate being engaged to the proximal side of the tibial MRD 800. The tibial MRD 800 can also include fin clearances 804 to permit rotation and position adjustment of the tibial baseplate. *Lateral member or lateral offset member 812 is connected to central body 810 at a lateral side thereof while medial member or medial offset member 814 is connected to central body 810 at a medial side thereof. Central body 810 and lateral and medial members 812, 814 are each conically shaped and each define a longitudinal axis depicted respectively as axes A, B, and C which are offset from each other in a lateral-medial direction, as shown in FIG. 12C.* The outer surfaces 806 of the tibial MRD 800 are configured to match the dimensions of surfaces of the bone 700 created by a particular cannulated reamer assembly 600. In this illustrative embodiment, outer surfaces 806 include three blended tapered conical surfaces that match the surface in the bone 700 created by the three reaming steps described above. *In this regard, outer surfaces 806 are curved surfaces that each extend/curve about longitudinal axis A, B, or C of the respective central body 810, lateral member 812, and medial member 814 and taper inwardly from a proximal end to a distal end of MRD 800. However, since axes B and C are angled inwardly toward axis A, as shown, curved outer surfaces 806 of lateral and medial members 812, 814 have a greater taper or slope than curved surface 806 of central body 810. Longitudinal axes A, B, and C correspond to the axes 720, 722 and 724 of the void formed by pockets 710, 712, and 714 shown in FIGS. 11D and 11E such that when MRD 800 is implanted into such void, axes A, B, and C align with axes 720, 722, and 724, respectively. Lateral and medial members 812, 814 are integrated into central body 810 such that the curved outer surfaces 806 of lateral and medial members 812, 814 respectively meet with outer surface 806 of central body 810 at an interfaces between the central body 810 and members 812 and 814. Such interfaces form indentations 808 that each appear as a longitudinally extending indented groove that extends in a proximal-distal direction along the entire length of the particular interface. As shown, lateral and medial members 812, 814 each*

*interface with central body 810 at two locations such that MRD 800 has four of such indentations 808, as best shown in FIG. 12A.*

Figure 13A:
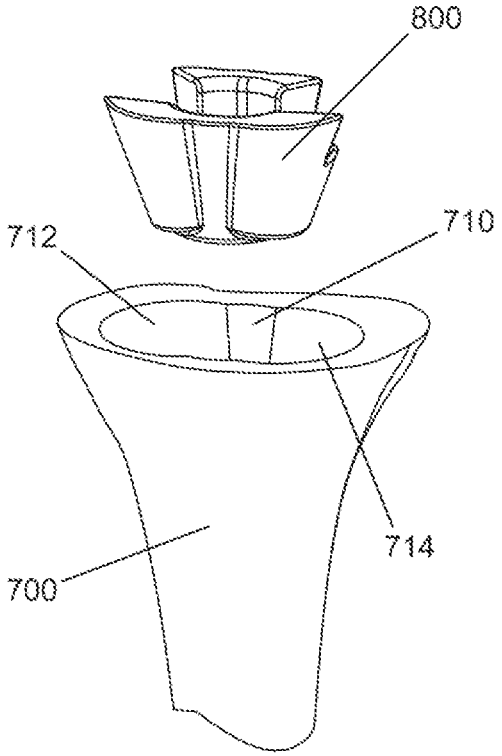
FIG. 13A shows a perspective view of the tibial metaphyseal reconstruction device shown in FIGS. 12A-D prior to implantation into a tibial bone.
Figure 13C:
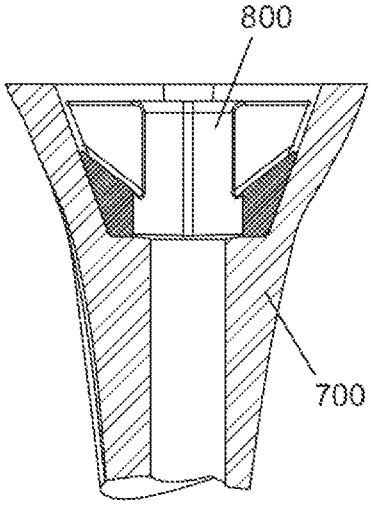
FIG. 13C shows a cross section view of the tibial bone after a metaphyseal reconstruction device has been implanted, taken along line 13C-13C of FIG. 13B.
Figure 13B:
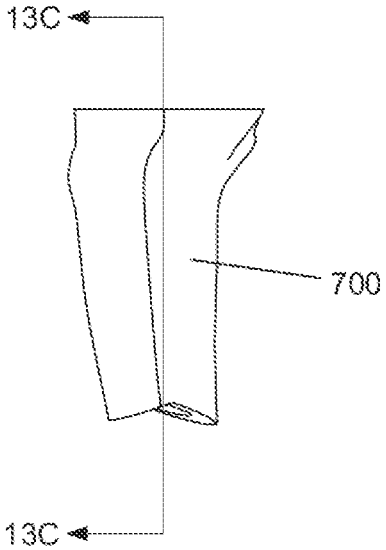
FIG. 13B shows a side view of the tibial bone after a metaphyseal reconstruction device has been implanted.

FIG. 13A shows the tibial MRD 800 prior to insertion into the void in the bone 700 consisting of the central pocket 710, the medial reaming void 712 and the lateral reaming void 714. FIG. 13B shows a side view of the bone 700 with the tibial MRD 800 inserted, along with section origin 13C. FIG. 13C shows a cross section along section origin 13C of the bone 700 with tibial MRD 800 inserted.

Figure 14A:
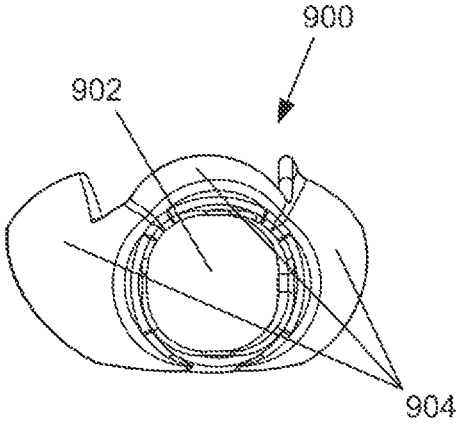
FIGS. 14A-D show different views of one embodiment of a femoral metaphyseal reconstruction device of the present invention.
Figure 14B:
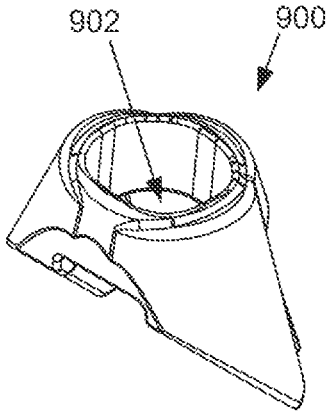
Figure 14C:
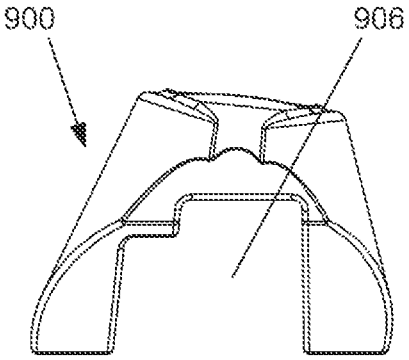
Figure 14D:
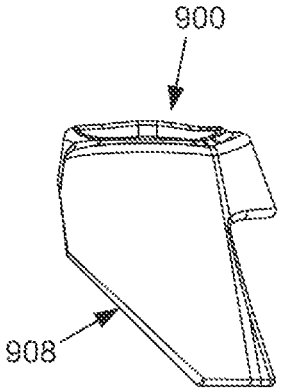
Figure 14E:
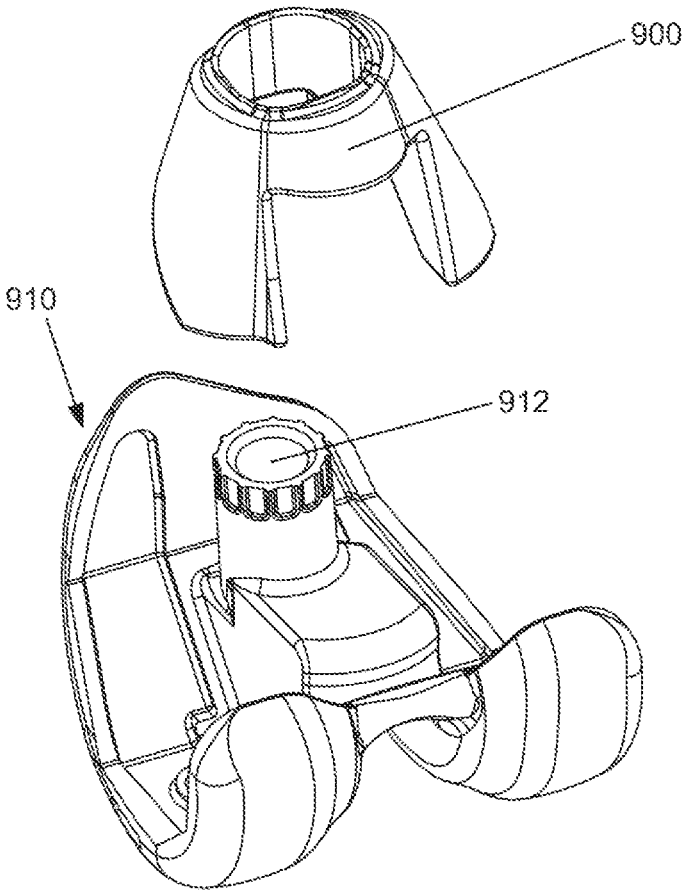
FIG. 14E shows a perspective view of the femoral metaphyseal reconstruction device shown in FIGS. 14A-D prior to attachment to a femoral implant.
Figure 14F:
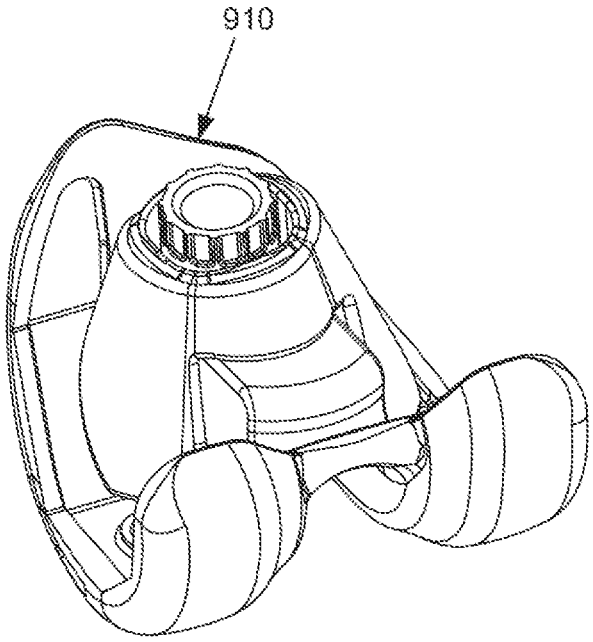
FIG. 14F shows a perspective view of the femoral metaphyseal reconstruction device after attachment to a femoral implant.

FIGS. 14A-D show, respectively, superior, isometric, anterior, and lateral views of an MRD. In this illustrative embodiment, the MRD is a femoral MRD 900. The femoral MRD 900 is generally similar to the tibial MRD 800, with the main difference being that the femoral MRD 900 is inserted into the bone void created by a reaming process on the distal end of the femur. The femoral MRD 900 includes a central opening 902 to allow for passage of a femoral stem. The femoral MRD 900 also can include tapered conical surfaces 904 to correspond to the particular shape of the bone voids created in the reaming process. Additionally, the femoral MRD 900 can include a first clearance space 906 for a femoral cam box, if needed, and a second clearance space 908 for the anterior chamfer of a femoral implant. FIGS. 14E and 14F show the femoral MRD 900 before and after attachment to the femoral implant 910, respectively. In this illustration, the femoral stem is omitted from the femoral stem attachment site 912 for clarity. The present invention can be used for multiple types of MRD implantation. For example, cemented MRDs can be used within the scope of this invention, in which there is a gap between the MRD and the balance of the implant construct, which is filled with bone cement during the procedure. Additionally, locked MRDs can be used within the scope of this invention, in which a mechanical connection, such as a taper lock, is made between the MRD and the balance of the implant construct.

There are many benefits of performing a revision procedure with the surgical reaming instrument of the present invention. For example, all bone removal steps may be fully guided without the need for any freehand bone removal. Additionally, the present invention provides a surgeon with the option of performing a guided ream of the bone either by hand or by using a powered source, such as a drill. Further, the instruments generally anatomically match typical bone voids observed in surgery. For example, the prepared cavity can be wider in the medial/lateral direction than in the anterior/posterior direction. Another related benefit is that the instrument has the capability to prepare asymmetric cavities, such as larger cavities on the medial side than the lateral side, which is often seen in cases of tibial bone voids. Importantly, because of the precision of control allowed when using this instrument, the shape of the cavity can be precisely controlled which allows for stock MRDs to accurately fit into the bone void without dependence on the technique of the particular surgeon performing the surgery. Related to this is that the symmetric, geometrically defined shape of the MRD simplifies the setup and machining of void fillers. Yet another benefit of an embodiment of this invention is that it allows a cannulated reamer set to consist of differently sized modular reaming heads and a single shaft to fit all reaming head sizes. This results in a reduced cost and size of the instrument set. The MRDs described herein can be made of any biocompatible material such as polymer and stainless steel, for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

[1. A surgical system for preparing bone comprising:

a reaming guide assembly including:

a trial stem having a proximal end and a longitudinal axis, the trial stem configured to fit into an intramedullary canal in the bone, and a guide tube assembly having a guide tube coupled to the proximal end of the trial stem such that a longitudinal axis of the guide tube is angled with respect to the longitudinal axis of the trial stem; and a cannulated reamer assembly for shaping a bone cavity, the cannulated reamer assembly having a proximal end, a reaming head coupled at a distal end and a cannulation extending through the reaming head and distal end thereof, wherein a longitudinal axis of the cannulated reamer assembly is angled with respect to the longitudinal axis of the trial stem when at least a portion of the guide tube is housed within the cannulation of the cannulated reamer assembly, and wherein the cannulated reamer assembly is both rotatable about and slidable along the guide tube during operation.]

[2. The surgical system of claim 1, wherein the proximal end of the cannulated reamer assembly is configured to engage a torque applying device.]

[3. The surgical system of claim 1, wherein the cannulated reamer assembly further comprises a quick connect mechanism having a ball detent engaged to a distal end of a reamer shaft, the ball detent selectively engaging a notch in a proximally protruding extension of the reaming head in order to couple the reamer shaft to the reamer head.]

[4. The surgical system of claim 1, wherein the reaming guide assembly further comprises a handle assembly for manipulating the reaming guide assembly, the handle assembly coupled to the proximal end of the trial stem such that a surgeon can manipulate the reaming guide assembly while the trial stem is located in the intramedullary canal.]

[5. The surgical system of claim 4, further comprising an insertion/removal tool for efficient removal of the reaming guide assembly from the bone canal, the insertion/removal tool having a distal end configured for selective engagement to the proximal end of the trial stem.]

[6. The surgical system of claim 4, wherein the guide tube assembly and the handle assembly are fixed with respect to each other and are rotatably mounted to the proximal end of the trial stem such that a surgeon may rotate the guide tube assembly and the handle assembly about the longitudinal axis of the trial stem while the guide tube assembly and the handle assembly partially reside within a central pocket in the bone.]

[7. The surgical system of claim 6, further comprising a tibial implant for implantation into the bone cavity prepared by the reaming guide and cannulated reamer assemblies, the tibial implant being shaped to match contours of the bone cavity and having a central opening defined therethrough, wherein the central opening is configured to permit the passage of the trial stem or a stem boss of a tibial baseplate into the intramedullary canal.]

[8. The surgical system of claim 7, wherein the shape of the tibial implant includes at least two outer surfaces being blended tapered conical surfaces that substantially match the contours of the bone cavity.]

[9. The surgical system of claim 8, wherein the tibial implant further comprises a proximal surface, a lateral wall, a medial wall and a fin clearance for positional adjustment of the tibial baseplate, the fin clearance defines a groove that extends from the lateral wall through the medial wall and extends through the proximal surface.]

[10. The surgical system of claim 6, further comprising a femoral implant for implantation into the bone cavity, the femoral implant being shaped to match contours of the bone cavity and having a central opening defined therethrough, wherein the central opening is configured to permit the passage of a femoral stem into the intramedullary canal.]

[11. The surgical system of claim 10, wherein the shape of the femoral implant includes at least two outer surfaces being tapered conical surfaces that substantially match the contours of the bone cavity.]

[12. The surgical system of claim 11, wherein the femoral implant further comprises a posterior wall, an anterior wall and a first and second clearance space, wherein the first clearance space defines a recess in the posterior wall shaped to accommodate a femoral cam box, wherein the second clearance space defines a cut in anterior wall shaped to accommodate an anterior chamfer of a femoral implant.]

[13. A surgical method for preparing bone comprising the steps of:

placing a reaming guide assembly at least partially into an already formed intramedullary canal and central pocket that is in fluid communication with the intramedullary canal, the reaming guide assembly comprising a trial stem and guide tube assembly, the trial stem having a proximal end configured to be received in the intramedullary canal, the guide tube assembly having a guide tube coupled to the proximal end of the trial stem such that a longitudinal axis of the guide tube is angled with respect to a longitudinal axis of the trial stem;

coupling a cannulated reamer assembly to the guide tube assembly such that the proximal end of the guide tube assembly is housed within a cannulation of the cannulated reamer assembly and the reaming head contacts bone at a first position; and driving the cannulated reamer along the guide tube to a predetermined depth into the bone, thereby forming a first reamed bone cavity adjacent to the central pocket.]

[14. The method of claim 13, wherein the reaming guide assembly further comprises a handle assembly, the handle assembly being fixed at the proximal end of the trial stem such that the handle assembly at least partially resides in the central pocket when the trial stem is fully seated in the intramedullary canal.]

[15. The method of claim 13, wherein the guide tube assembly is rotatably mounted to the proximal end of the trial stem such that the guide tube assembly can be rotated about the trial stem from the first position to a second position.]

[16. The method of claim 15, further comprising the step of rotating the handle assembly and guide tube assembly to the second position while partially residing within the central pocket.]

[17. The method of claim 16, further comprising the step of reaming bone at the second position with the cannulated reamer assembly placed over the guide tube assembly, thereby forming a second reamed bone cavity adjacent to the central pocket.]

[18. A method for preparing bone to receive a revision prosthesis comprising the steps of:

reaming the bone generally along an intramedullary canal with an intramedullary reamer having a proximal end;

placing a cannulated reamer assembly having a reaming head over the proximal end of the intramedullary reamer such that the reaming head contacts the bone;

driving the cannulated reamer into bone to a predetermined depth, thereby forming a central bone pocket;

removing the intramedullary reamer and cannulated reamer assembly from the intramedullary canal and central bone pocket;

placing a reaming guide assembly at least partially into the intramedullary canal and central bone pocket; wherein the reaming guide assembly comprises a trial stem, a guide tube assembly, and a handle assembly, the trial stem having a proximal end and being configured to fit into the intramedullary canal, the guide tube assembly having a proximal end and distal end that is rotatably fixed to the proximal end of the trial stem at an oblique angle such that the guide tube assembly at least partially resides in the central bone pocket when the trial stem is fully seated in the intramedullary canal, the handle assembly being fixed at the proximal end of the trial stem such that the handle assembly at least partially resides in the central bone pocket when the trial stem is fully seated in the intramedullary canal;

placing the cannulated reamer assembly over the proximal end of the guide tube assembly such that the reaming head contacts bone at a first position; and driving the cannulated reamer into bone to a predetermined depth, thereby forming a first bone cavity adjacent to the central bone pocket.]

[19. The method of claim 18, further comprising the step of rotating the handle assembly and guide tube assembly with respect to the trial stem while partially residing within the central pocket to a second position.]

[20. The method of claim 19, further comprising the step of reaming bone at the second position with the cannulated reamer assembly placed over the guide tube assembly, thereby forming a second bone cavity adjacent to the central pocket.]

[21. The method of claim 13, further comprising:

disengaging a pin located at a distal end of the guide tube assembly from a first notch disposed at a first location about the trial stem;

rotating the guide tube assembly about the trial stem; and engaging the pin with a second notch disposed at a second location about the trial stem.]

*22. A method of implanting a tibial prosthesis in a total knee revision arthroplasty, comprising:*

*removing a previously implanted tibial prosthesis from a proximal end of a tibia; and*

*implanting a void filler into the proximal end of the tibia, the proximal end of the tibia having a bone void previously formed by a surgical instrument so as to form a central pocket and lateral and medial pockets blended into the central pocket, the central pocket and lateral and medial pockets having been formed to correspond to a geometry of the void filler so that when the void filler is implanted, a central body of the void filler is received in the central pocket, lateral and medial members of the void filler are respectively received in the lateral and medial pockets, and an opening extending entirely through the central body of the void filler communicates with an intramedullary canal of the tibia, wherein the central body and lateral*

*and medial members each have a curved outer surface that extends about a respective longitudinal axis, the curved outer surface of each of the lateral and medial members tapering inwardly from a proximal end of the void filler to a distal end thereof, the lateral member being integrated into the central body such that the curved outer surfaces of the lateral member and the central body meet at an interface between the lateral member and central body, the interface forms an indented groove that extends in a proximal-distal direction along an entire length of the interface.*

*23. The method of claim 22, further comprising connecting the void filler to a baseplate component, wherein the void filler is constructed separately from the baseplate component.*

*24. The method of claim 23, wherein connecting the void filler to the baseplate component includes inserting a stem boss of the baseplate component into the opening extending through the central body of the void filler.*

*25. The method of claim 23, wherein connecting the void filler to the baseplate component includes inserting a tibial stem through the opening of the central body of the void filler.*

*26. The method of claim 25, further comprises implanting the baseplate component onto the proximal end of the tibia such that the tibial stem extends from the opening of the central body and into the intramedullary canal and such that the baseplate component engages a proximal end of the void filler.*

*27. A method of implanting a tibial prosthesis in a total knee revision arthroplasty, comprising:*

*removing a previously implanted tibial prosthesis from a tibia;*

*forming a bone void in the tibia at a proximal end thereof so as to form a central portion and adjacent offset portions of the bone void, the offset portions joining the central portion and tapering inwardly from the proximal end of the tibia toward a distal end thereof, wherein forming at least one of the offset portions of the void includes moving a cutting tool axially along a longitudinal axis into the bone and removing the cutting tool from the bone by moving the cutting tool along the same longitudinal axis, the cutting tool being constrained to movement along the longitudinal axis; and*

*implanting a void filler and a revision tibial prosthesis onto the proximal end of the tibia such that a central body and adjacent offset members of the void filler are respectively and conformingly disposed in the central and offset portions of the bone void, and such that a stem of the revision tibial prosthesis extends through an opening of the central body and a baseplate component of the revision tibial prosthesis is positioned adjacent a proximal end of the void filler and the proximal end of the tibia, wherein the offset members of the void filler and the central body each define a longitudinal axis about which a respective curved exterior surface thereof extends, the longitudinal axes of the offset members and void filler being offset in a lateral-medial direction.*

*28. The method of claim 27, further comprising mechanically locking the void filler to the revision tibial prosthesis.*

*29. The method of claim 27, further comprising inserting bone cement into a gap between the void filler and the tibial prosthesis so as to connect the void filler to the tibial prosthesis.*

*30. The method of claim 27, further comprising:*

*inserting a stem boss of the baseplate component of the tibial prosthesis into the opening of the central body, and*

*engaging a proximal end of the void filler with the tibial baseplate.*

*31. The method of claim 27, wherein forming the bone void is performed by an instrument having bone cutting surfaces that correspond to the central body and offset members of the void filler so that a peripheral geometry of the void filler matches surfaces in the tibia created by the instrument.*

*32. The method of claim 31, wherein the instrument is a reamer assembly.*

*33. The method of claim 27, wherein the offset members are conically tapered and have a taper greater than a taper of the central portion.*

* * * * *